(12) United States Patent
Virtanen

(10) Patent No.: US 6,274,373 B1
(45) Date of Patent: Aug. 14, 2001

(54) GENE SEQUENCER AND METHODS

(75) Inventor: Jorma Virtanen, Irvine, CA (US)

(73) Assignee: Burstein Technologies, Inc., Irvine, CA (US)

( * ) Notice: Subject to any disclaimer, the term of this patent is extended or adjusted under 35 U.S.C. 154(b) by 0 days.

(21) Appl. No.: 09/564,399

(22) Filed: May 1, 2000

Related U.S. Application Data

(63) Continuation of application No. 09/064,635, filed on Apr. 21, 1998, now abandoned, and a continuation of application No. PCT/US98/03362, filed on Feb. 20, 1998.
(60) Provisional application No. 60/039,027, filed on Feb. 21, 1997.

(51) Int. Cl.[7] .............................. C12M 1/00; C12Q 1/68; C12P 19/34; C07H 21/04; H04N 5/85
(52) U.S. Cl. ........................ 435/285.1; 435/6; 435/91.1; 435/91.2; 435/283.1; 435/285.2; 435/287.2; 536/23.1; 536/24.3; 536/24.31; 536/25.32; 386/124

(58) Field of Search ..................... 435/6, 91.1, 91.2, 435/283.1, 285.1, 285.2, 287.2; 536/23.1, 24.3, 24.31, 24.32, 25.32; 386/124

(56) References Cited

U.S. PATENT DOCUMENTS

| 5,412,087 | 5/1995 | McGall et al. ..................... 536/24.3 |
| 5,863,708 | * 1/1999 | Zanzucchi ......................... 430/320 |

FOREIGN PATENT DOCUMENTS

| 0 721 062 A2 | 7/1996 | (EP) . |
| WO 95/00530 | 1/1995 | (WO) . |
| WO 95/09248 | 4/1995 | (WO) . |
| WO 98/01533 | 1/1998 | (WO) . |

* cited by examiner

Primary Examiner—Kenneth R. Horlick
Assistant Examiner—Jeffrey Siew

(57) ABSTRACT

A gene sequencer, bio-compact disk and sample preparation methodology is described. Constant length oligonucleotides are prepared and, in conjunction with the bio-compact disk and apparatus described, used in gene sequencing and strategies therefor.

18 Claims, 18 Drawing Sheets

SPACER   OLIGONUCLEOTIDE, n-mer

SYNTHETIC MIXTURE OF ALL n-MERIC OLIGOS WITH LABEL

SAMPLE OLIGOS (n-mers) FROM ONE SPHERE

FIG. 12

In genome:

GGTTAAAAAAAACCCC And CCCCAAAAAAAATTTT
(Gene Sequence)           (Gene Sequence)
       #1                        #2

THE FOLLOWING 8-MERS ARE RECOGNIZED:

```
GGTT AAAAAAAA CCCC              CCCC AAAAAAAA TTTT

GGTT AAAA                       CCCC AAAA
 GTT AAAAA                       CCC AAAAA
  GT AAAAAA                       CC AAAAAA
   T AAAAAAA                       C AAAAAAA
     AAAAAAAA                        AAAAAAAA
     AAAAAAA C                       AAAAAAA T
      AAAAAA CC                       AAAAAA TT
       AAAAA CCC                       AAAAA TTT
        AAAA CCCC                       AAAA TTTT
```

THIS DATA GIVES TWO POSSIBILITIES:

GGTT AAAAAAAA CCCC AND CCCC AAAAAAAA TTTT

OR

GGTT AAAAAAAA TTTT AND CCCC AAAAAAAA CCCC
 (Gene Sequence)        (Gene Sequence)
       #3                     #4

FIG. 13

In genome:

GGGG AAAA TTATT AAAA CCCGG AND CCCC AAAA GGTGG AAAA GGGCC
  *(Gene Sequence)*               *(Gene Sequence)*
        #5                              #6

RESULTING RECOGNITION PATTERNS:

```
GGGG AAAA TTATT AAAA CCCGG        CCCC AAAA GGTGG AAAA GGGGCC
GGGG         TATT                 CCCC         GTGG
 GGG A       ATT A                 CCC A       TGG A
  GG AA       TT AA                 CC AA       GG AA
   G AAA      T AAA                  C AAA      G AAA
    |AAAA      AAAA|                  |AAAA      AAAA|
     AAA T      AAA C                  AAA G      AAA G
      AA TT      AA CC                  AA GG      AA GG
       A TTA     A CCC                   A GGT     A GGG
         TTAT    CCCG                     GGTG     GGGC
         TATT    CCGG                     GTGG     GGCC
```

THIS DATA GIVES UNAMBIGUOUS SEQUENCES:

GGGG AAAA TTATT AAAA CCCGG AND CCCC AAAA GGTGG AAAA GGGCC

THESE ARE SAME AS IN GENOME

EXAMPLE OF DEGENERACY IN (4,{5},4)-RECOGNITION

GENE SEQUENCER AND METHODS

This application is a continuation of Ser. No. 09/064,635, Apr. 21, 1998, now abandoned, which claims benefit of Ser. No. 60/039,027 Feb. 21, 1997 and a continuation of PCT/US98/03362 Feb. 20, 1998.

FIELD OF THE INVENTION

This invention relates generally to the field of gene sequencing. More particularly, this invention relates to a gene sequencer, a high density bio-compact disk useful therewith and a method of sample preparation therefor. The high-density bio-compact disk and the sample preparation methodology find application in the field of oligonucleotide sequencing and DNA sequencing and detection generally.

SUMMARY OF THE INVENTION

In one aspect, the present invention features a sample preparation method for obtaining n-mer oligonucleotides from a sample containing oligonucleotide fragments comprising: (a) forming a solid support having all possible n-mer oligonucleotides attached to the surface of the support; (b) contacting the solid support resulting from step (a) with the sample under conditions causing the sample oligonucleotides to hybridize with the complementary n-mer oligonucleotides on the solid support; (c) contacting the solid support resulting from step (b) with a hydrolyzing agent; (d) separating the unbound oligonucleotides from the hybridized oligonucleotides; and (e) denaturing the hybridized n-mer oligonucleotides to obtain the n-mer oligonucleotides of the sample; wherein n is an integer selected from the integers 4–10,000, most advantageously 6–28.

In another aspect, the invention features a method of obtaining n-mer oligonucleotides from a sample containing oligonucleotide fragments comprising: (a) contacting a solid support adapted to couple with oligonucleotides in the sample with at least a portion of the sample; (b) contacting the solid support resulting from step (a) with a mixture of n-mer oligonucleotides for a time sufficient for the n-mer oligonucleotides to hybridize with the complementary n-mer oligonucleotides on the solid support; (c) separating the hybridized n-mer oligonucleotides from the unhybridized oligonucleotides; (d) denaturing the hybridized n-mer oligonucleotides to obtain the n-mer oligonucleotides complementary to those present in the sample; wherein n is an integer selected from the integers 4–10,000, most advantageously 6–28.

In still another aspect, the sample preparation method includes a method of obtaining n-mer oligonucleotides from a sample containing oligonucleotide fragments comprising: (a) contacting a solid support having bound thereon oligonucleotides from a sample with a mixture of a plurality of oligonucleotides having (k+m)-mers, wherein k+m=n, with a mixture of a plurality of first oligonucleotides, each being a k-mer and being without a free hydroxyl group at the 3'-end thereof, and a plurality of second oligonucleotides, each being a m-mer and being without a free phosphate group at the 5'-end thereof; (b) ligating the oligonucleotides on the solid support resulting from step (a); (c) removing the unligated oligonucleotides from the solid support; and (d) denaturing the hybridized n-mer oligonucleotides remaining on the solid support to obtain the n-mer oligonucleotides complementary with those present in the sample; wherein m, k and n are each an integer selected from the integers from 6–10,000, most advantageously 12–40, with the proviso that k+m=n.

In yet another aspect, the sample preparation method includes a method of obtaining n-mer oligonucleotides from a sample containing oligonucleotide fragments comprising: (a) contacting a solid support having bound thereon a plurality of oligonucleotides from a sample with a mixture of a plurality of h-mer oligonucleotides each having a phosphate group at both the 3'- and 5'-end, a plurality of i-mer oligonucleotides each having a hydroxyl, amino or thiol group at the 3'-end and no terminal phosphate group, and a plurality of j-mer oligonucleotides having a hydroxyl, amino or thiol group at the 5'-end and no terminal phosphate group; (b) chemically or enzymatically ligating the oligonucleotides on the solid support resulting from step (a); (c) removing the unligated oligonucleotides from the solid support resulting from step (b); and (d) denaturing the hybridized n-mer oligonucleotides remaining on the solid support to obtain the n-mer nucleotides complementary with those present in the sample; wherein h, i and j are each an integer selected from the integers from 6–10,000, most advantageously 18–60, with the proviso that h+i+j=n.

In yet another aspect of this invention, an assay element is described comprising a substrate having a surface including a plurality of discrete areas on the surface adapted to attach to a spacer molecule; a plurality of spacer molecules attached at a first end to said surface in each of the discrete areas, each of said spacer molecules adapted to being attached at its second end to a metallic surface or a label, each of said spacer molecules having a site between its first end and its second end capable of being cleaved; a first n-mer oligonucleotide having a first sequence attached to substantially all of the spacer molecules between the cleavage site and the first end of the spacer molecule, and a second n-mer oligonucleotide having a second sequence attached to substantially all of the spacer molecules; wherein substantially no other discrete areas on the surface of the substrate contain spacer molecules having n-mer oligonucleotides having the first sequence attached thereto and n is an integer selected from the integers 4–10,000, most advantageously 6–28.

The present invention also encompasses a method for determining the sequence of a (p+q+r)-mer segment of a gene suspected of being present in a sample comprising: (a) forming a solution of the sample and a mixture of q-mer oligonucleotides having all possible sequences of a q-mer oligonucleotide, or, optionally, a subset of all such possible sequences; (b) contacting an assay element with at least a portion of the solution of step (a), the assay element having a surface and plurality of spacer molecules bound to the surface, the spacer molecules having a first end bound to the surface and a second end bound to a metallic surface or a label and a cleavage site intermediate between the first and second ends, the spacer molecules further having a first p-mer oligonucleotide attached thereto between the cleavage site and the first end and a second r-mer oligonucleotide attached thereto between the cleavage site and the second end, the combination of p-mers and r-mers including all combinations of oligonucleotide sequences of p-mer and r-mer oligonucleotides, or, optionally, a subset of all such combinations, each particular combination of sequences of the p-mer and r-mer oligonucleotides being at a predetermined location on the surface; (c) ligating the resultant hybridized oligonucleotides attached to the spacer molecules resulting from step (b) above; (d) detecting the presence or absence of a particular sequence combination of the hybridized oligonucleotides at each predetermined location on the surface; and (e) processing the sequence information obtained from step (d) to deduce the sequence of the (p+q+r)-mer oligonucleotide present in the sample, wherein p, q and r are integers selected from the integers 4–10,000, most advantageously 6–26, and (p+q+r) does not exceed 30,000, and most advantageously 60. Steps (a)–(e) can be performed in parallel for different, multiple segments of a gene.

BRIEF DESCRIPTION OF THE DRAWINGS

The invention will be better understood by reference to the following drawings in which:

FIG. 12 is an illustration of (4,4)-mer recognition used to determine sequencing information relating to a gene fragment.

FIG. 13 is an illustration of (4,{5},4)-mer recognition used to determine sequencing information relating to a gene fragment.

DETAILED DESCRIPTION OF THE INVENTION

Significant background information as well as additional guidance for practicing particular embodiments of the present invention within the scope of the appended claims may be found in PCT/US97/11826, now available publicly in published form, the disclosure of which is herein expressly incorporated by reference.

SAMPLE PREPARATION

Oligonucleotide arrays hold great promise in gene sequencing. Presently these methods are mostly limited to gene checking wherein the sequence is known except at some specific points, and only a limited set of oligonucleotides is needed in the array. De novo sequencing is more difficult, because very large arrays, containing all possible constant length oligonucleotides, are difficult to produce. Also, random length sample oligonucleotides cause complications. They can hybridize with each other with stronger bonding than with the probe oligonucleotides. Optimum length oligonucleotides hybridize more quickly and with greater fidelity than oligonucleotides that are too long. The present invention describes four methods that can be used to prepare uniform length oligonucleotides from any DNA sample. Moreover, these methods can be used so that the processed sample contains all essential uniform length oligonucleotides, which do not have a complementary oligonucleotide in the mixture, i.e., they cannot form any duplexes. This is a great advantage in oligonucleotide array methods, which are all based on the hybridization between sample and probe oligonucleotides. Hybridization is prevented by limiting, for example, the central nucleotide to adenosine or cytosine (AC-constraint) in all uniform length sample oligonucleotides. Thus, two sample oligonucleotides are not able to hybridize with each other and are instead able to hybridize completely only with the probe oligonucleotides in the array.

Polymerase Chain Reaction (PCR) is a highly effective DNA amplification method. PCR, however, has serious drawbacks when applied in oligonucleotide array methods and in massive de novo sequencing, such as the sequencing of a whole chromosome at one time. In order to use PCR, short primers are needed to initiate the reaction. To completely cover the chromosome with primers, a significant part of the sequence must be known with certainty. Also, each cycle in PCR tends to give shorter oligonucleotides than the previous one. Taken together these features mean that various segments of the chromosome are unevenly represented and some parts may be not be represented at all after PCR amplification of an unknown sample.

Ligase Chain Reaction (LCR) provides uniform length oligonucleotides when the sequence is known. One method described in this application is an extension of the LCR for the general case that does not need any prior knowledge of the sequence.

Figure 10A:
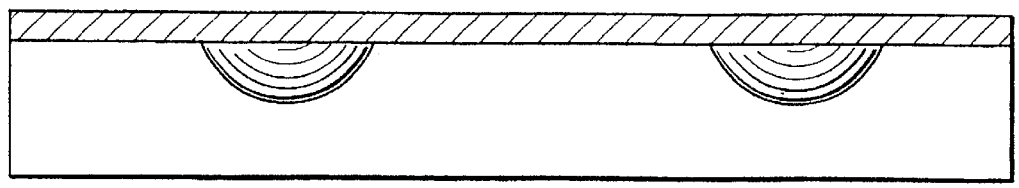
FIGS. 10A–10B schematic representations of a stamp that has hydrophilic cavities in a hydrophobic surface.
Figure 10B:
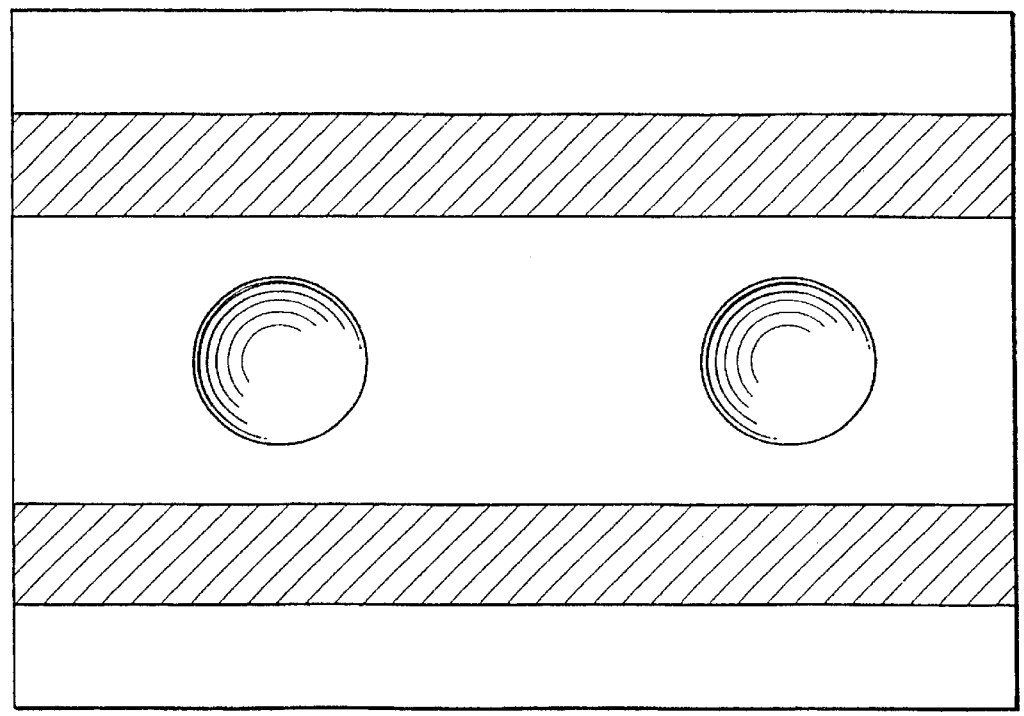
Figure 11A:
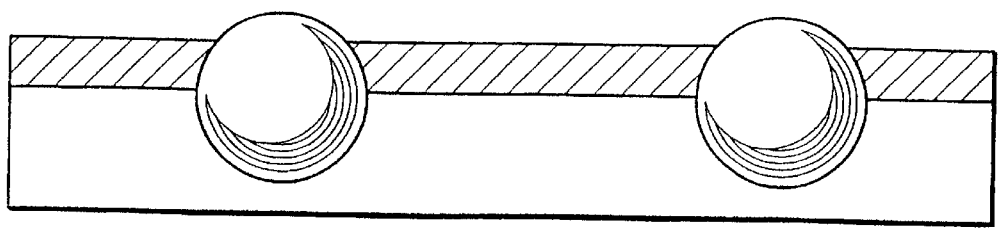
FIGS. 11A–11B are schematic representations of a stamp in FIG. 10 where latex spheres are chemically bound in the cavities.
Figure 11B:
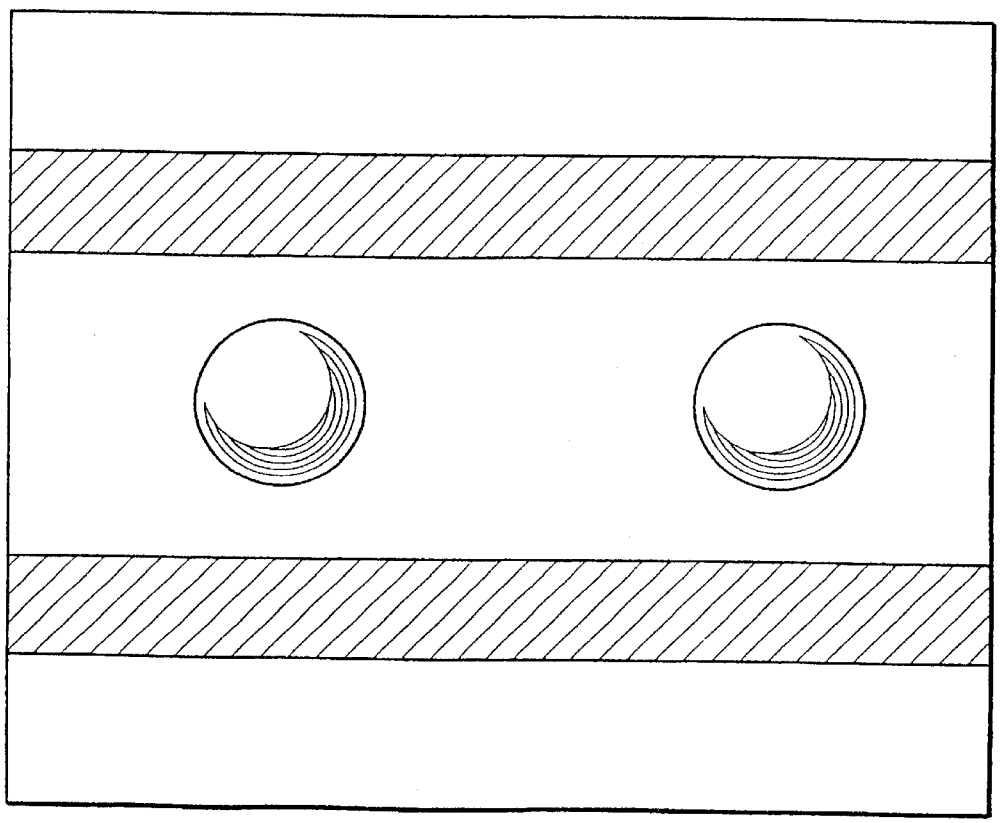

De novo sequencing requires high density arrays. These previously have been produced by lithographic methods. Despite that use, this method requires sophisticated instrumentation and can result in the formation of a significant amount of impurities. In this application two simple printing methods are described which allow micrometer accuracy. As illustrated in FIGS. 10 and 11, the first utilizes immobilized porous latex spheres on a hydrophobic surface. The latex spheres can be wetted with a chemical solution, such as an oligonucleotide in water, and pressed against another surface that is capable of binding one of the components (oligonucleotide). This method requires generally multiple printing steps, but it is useful for the fabrication of a master stamp for complementary printing. The complementary stamp is chemically patterned so that it can bind from a complicated mixture a certain component to a specified site. The stamp can contain millions of different sites for various components. After washing, all unbound components are removed, and the stamp is brought into contact with a surface that is able to chemically bind the desired components. The components are detached from the stamp, allowed to diffuse in a channel and to react with the active surface. Thus, millions of chemical components, such as oligonucleotides, can be transferred with micrometer accuracy in one printing step. By repeating the process a combination of billions of oligonucleotide pairs can be created. No other methods, lithographic, ink-jet or conventional printing allows one to fabricate such a high-density pattern in just two steps. Moreover, no sophisticated instrumentation is needed.

High resolution printing of one chemical at a time is well known. Also, chemical printing whereby various chemicals are fed onto the surface along channels is well known. The latter method actually allows production of arrays, but the density is not very great. Due to flow requirements the capillaries cannot be too narrow. Although thousands of such capillaries could possibly be on one stamp, it is not conceivable that millions of flow capillaries could be in any reasonably sized surface. On the other hand, millions of micrometer scale channels can be stamped onto plastic. These channels may be rendered hydrophilic and each of them coated with a certain oligonucleotide using either photolithography or, preferably, a set of latex sphere stamps described separately in this application.

An oligonucleotide array that would be able to sequence one human chromosome unequivocally would be overwhelming to fabricate. So far the oligonucleotide arrays have been able to de novo sequence about 2000 base pairs (bps). Sequence checking can be performed for much longer sequences, for example 20,000 bps. One chromosome can contain 250 million bps, which is about 100,000 times more than can be conveniently sequenced by present oligonucleotide arrays. The sample preparation methods and high-density bio-compact disks described in this application greatly improve sequencing. However, the proper sequencing protocol is fundamentally important to obtain reliable results while minimizing the number of bio-compact disks that must be used.

The approach taken in this application is as follows: 1) determine all 16-mer oligonucleotides that are part of a chromosome; and 2) determine both 8-mer ends of all 27-mer oligonucleotides without knowing the middle 11-mer sequence of these 27-mers. Actual numbers are only examples and several variations of this approach are possible. These two sets of data can be acquired with a similar set of bio-compact disks, i.e. disks that use (8,8) recognition. Data set 1 (all 16-mers) allows one to determine the central 11-mer sequence in each 27-mer of data set 2. Thus, all 27-mer sequences that are part of the overall sequence will be known. This allows almost unequivocal deduction of the original sequence. Only some long repeat sequences are outside the capability of this method. Even in those cases, the alternative sequences are known. Custom-made oligonucleotide arrays may be needed to conclusively deduct long repeat sequences.

In all bio-chip array DNA assays, the stationary oligonucleotides are of a certain length, i.e., they are m-mers wherein m is a fixed number between 8 and 30 in a given bio-chip array. The sample is prepared by random hydrolysis, either chemically or enzymatically. The sample contains oligonucleotides that have variable length. However, in order to avoid over-hydrolysis, the targeted length is about 50 bases (50-mer). The excessive and variable length slows down the hybridization and may lead to unwanted interactions. The ideal sample contains constant length oligonucleotides, n-mers, where n is equal to or slightly larger than the length of the stationary oligonucleotides, which are m-mers ($n \geq m$). Four variations of a procedure that gives sample oligonucleotides having constant and desired lengths are described below.

METHOD 1

Figure 1:
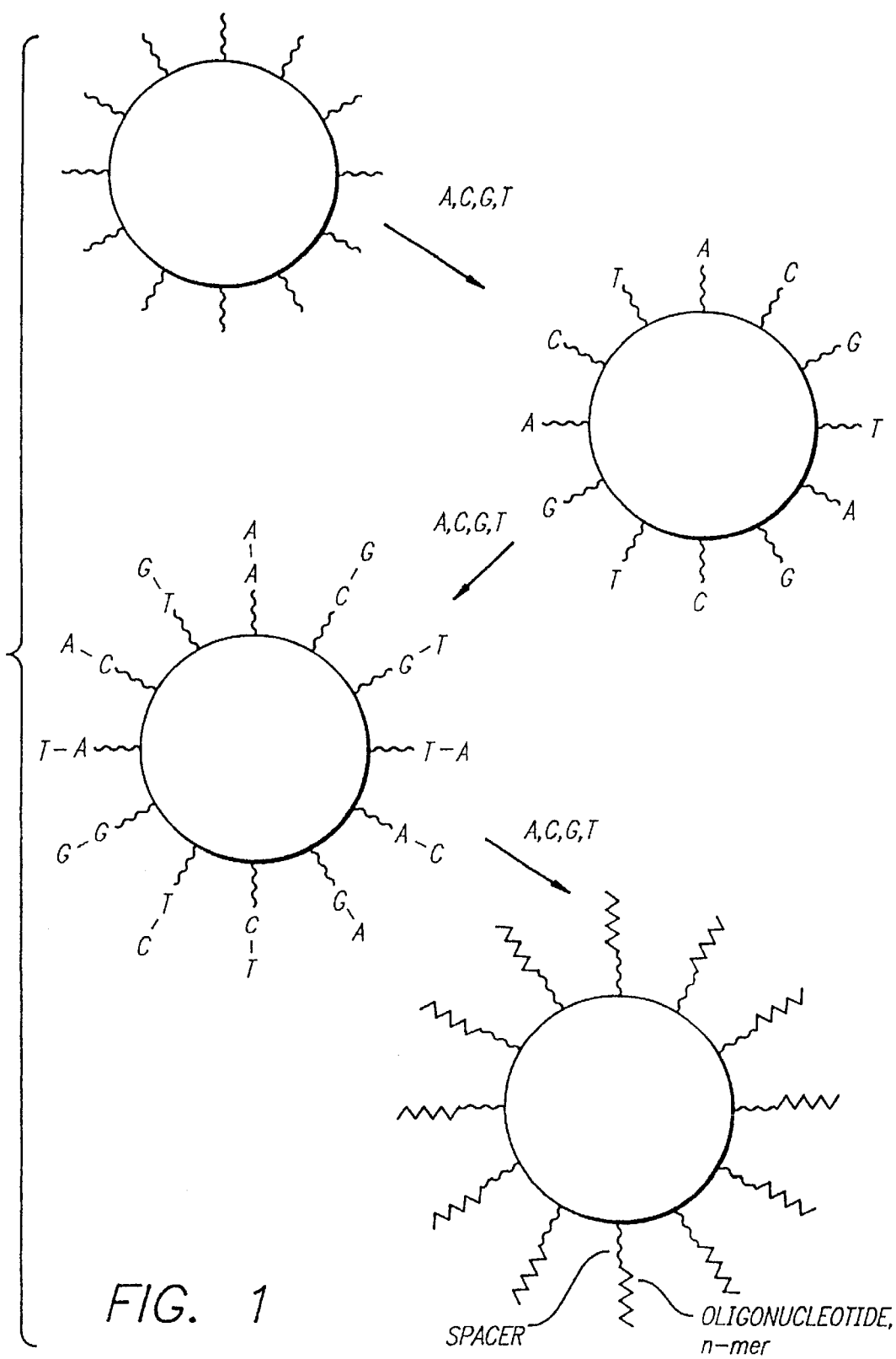
FIG. 1 is a schematic representation of the synthesis of a plurality of n-mer oligonucleotides on a solid support.
Figure 2:
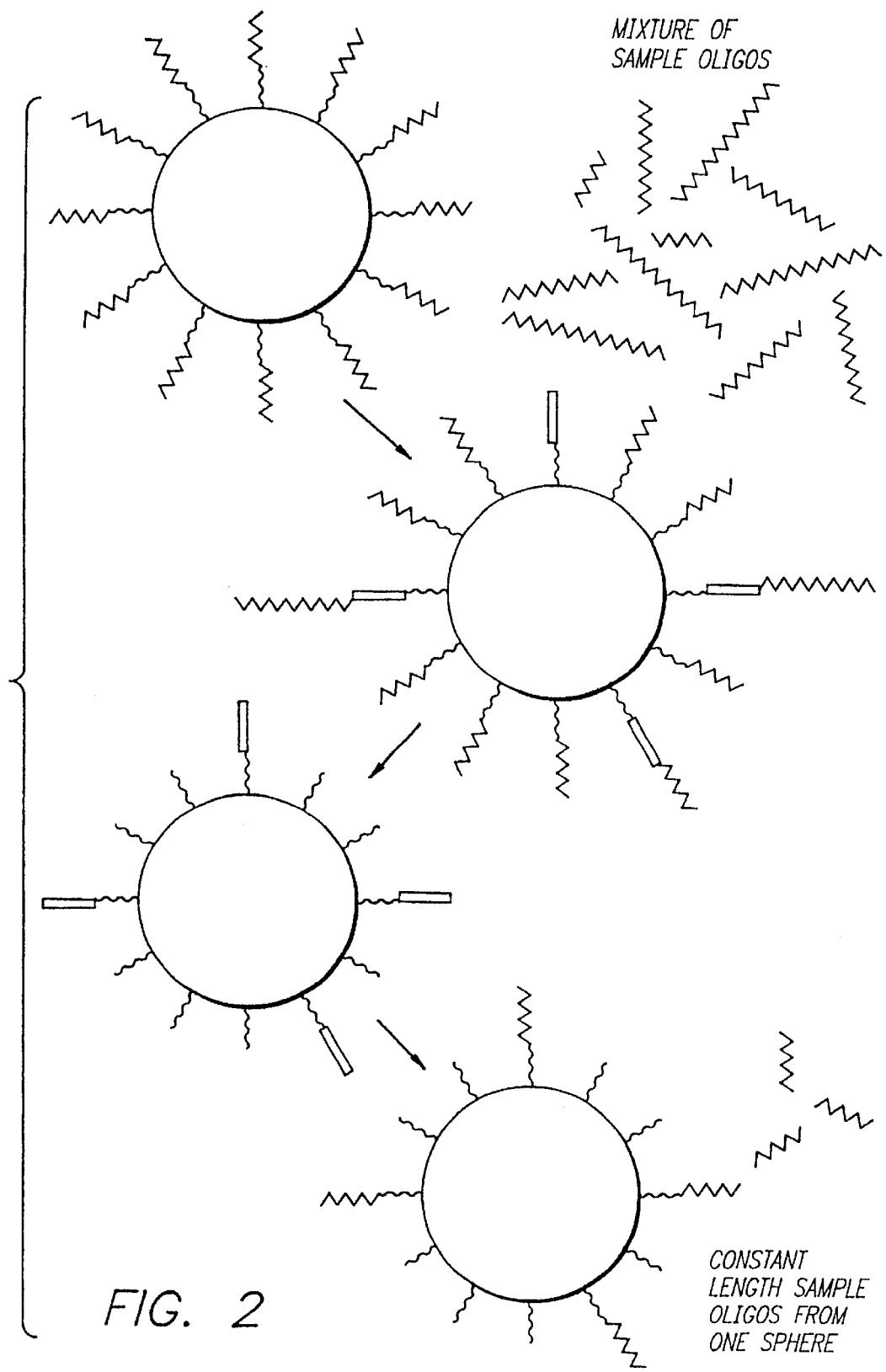
FIG. 2 is a schematic representation of a method using the solid support of FIG. 1 to select n-mer oligonucleotides from a sample containing a mixture of oligonucleotides of variable n-mer length.

(Nuclease S. FIG. 1: Synthesis of a complete mixture of n-mers; FIG. 2: Preparation of n-mers from oligomers of variable length; and FIG. 3: Linear amplification).

First, all possible oligonucleotide n-mers are synthesized on a solid support. This is easily achieved by using, at each coupling step, an equimolar mixture of adenosine, cytosine, guanosine and thymidine phosphoramidites or other derivatives of these nucleotides. Two synthetic steps are depicted in FIG. 1. After n coupling steps all n-mers are on the chosen solid support. A complete mixture of oligonucleotides up to 26-mer can be practically synthesized by this method. Table 1 demonstrates the number of molecules of a certain oligonucleotide n-mer in 10 milligrams of the mixture (the weight of the support is not included).

There is a certain statistical fluctuation in the amounts of the various n-mers in the mixture. For 28-mers it is expected that several possible oligonucleotides are not represented at all in the 10-milligram mixture while some others have more than 20 copies so that the average number of copies is 11. The fluctuation is insignificant for 24-mers, because all possible 24-mers have more than $2*10^3$ copies in the 10-milligram mixture, and that is thus a complete mixture.

The sample oligonucleotide fragments are hybridized with the complete mixture of n-mers bound onto the solid support (FIG. 2). A hydrolyzing agent, such as Nuclease S, which hydrolyzes single-stranded DNA, is added. Only the hybridized oligonucleotide segments are protected against hydrolysis. The overhangs of the sample oligonucleotides are largely removed. Also the stationary n-mers on the solid support which do not have matching oligonucleotides in the sample are hydrolyzed (FIG. 2). Hydrolysis does not need to be ideally complete in order to be useful. For example, if n is 16, the useful range of sample oligonucleotides is between 16 and 22-mers when using the bio-compact disk. Similarly, if stationary n-mers are only partially hydrolyzed, the remaining n-mers can be used for the amplification of the sample.

The solid support contains, after hydrolysis, such as with Nuclease S treatment, a stationary set of n-mers, which are complementary to the sample oligonucleotides. By hybridizing a complete soluble n-mer mixture with this stationary set of n-mers as shown in FIG. 2, a complete copy of sample n-mers is obtained. The process can be repeated several times, but it is inefficient because the amplification is a linear function of the time and effort. This process can be modified to be exponential by PCR amplification or analogous methods well known in the art.

If base selection is constrained in a certain site of the n-mers, the number of molecules is correspondingly larger. For example, if in the center of these oligonucleotides only adenosine and cytidine are allowed (AC-constraint), the number of copies for each n-mer is twice the number given in Table 1. The base limitation is achieved by using, in a specified step, a mixture of appropriate adenosine and cytidine derivatives. AC-constrained 25-mers are a compromise that allows practical sample preparation and reliable sequencing.

Figure 3:
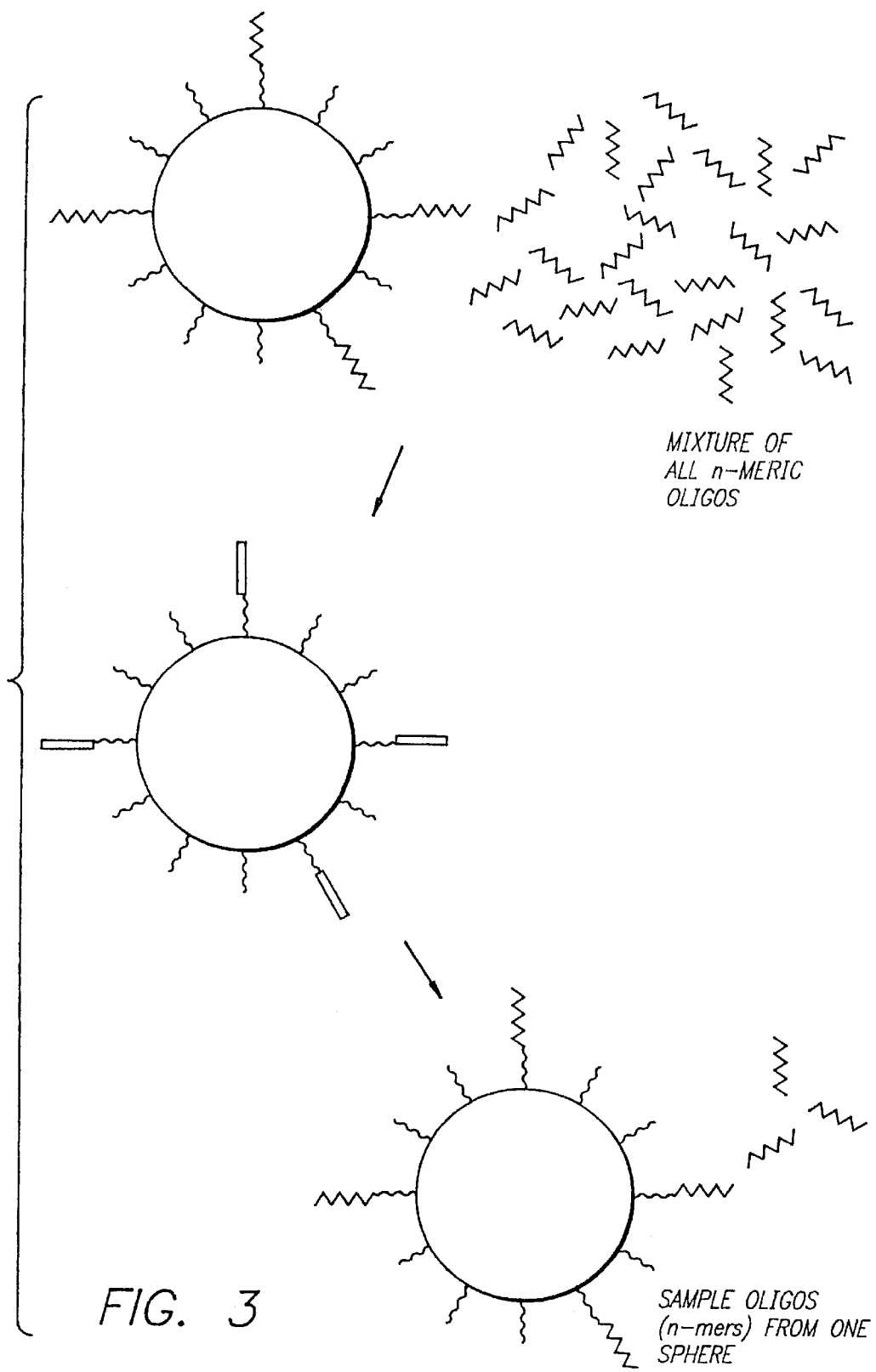
FIG. 3 is a schematic of a linear amplification to obtain a sample of n-mer oligonucleotides using a solid support.
Figure 4:
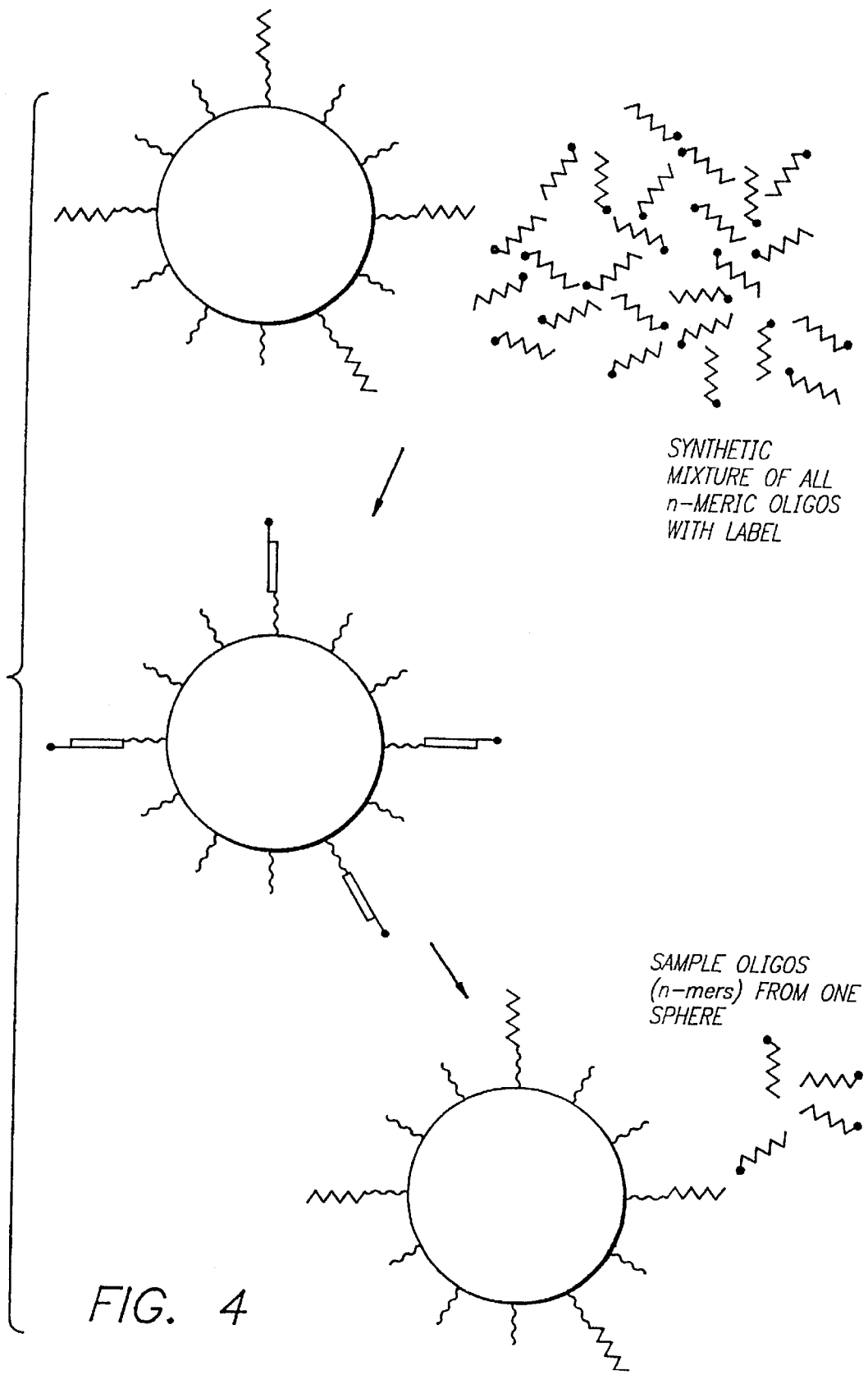
FIG. 4 is a schematic representation of the amplification to obtain a sample of labeled oligonucleotides.

METHOD 2
(Hybridization only; FIGS. 3 and 4: Amplification of labeled or activatable n-mer oligonucleotides)

Instead of attaching a complete mixture of oligonucleotides to a solid support, a fragmented sample of oligonucleotides may be attached to it. The solid support can be silica particles, magnetic spheres or capillaries. The bound sample is treated with a complete mixture of n-mers, which can optionally contain a label (such as fluorescein or an enzyme) or a reactive functional group (such as a thiol). Unhybridized oligonucleotide n-mers are washed away. By heating, the hybridized n-mers are removed and collected to provide a set of n-mer oligonucleotides that are complementary to the n-mer oligonucleotides of the sample. The process can be repeated as many times as needed.

Figure 5:
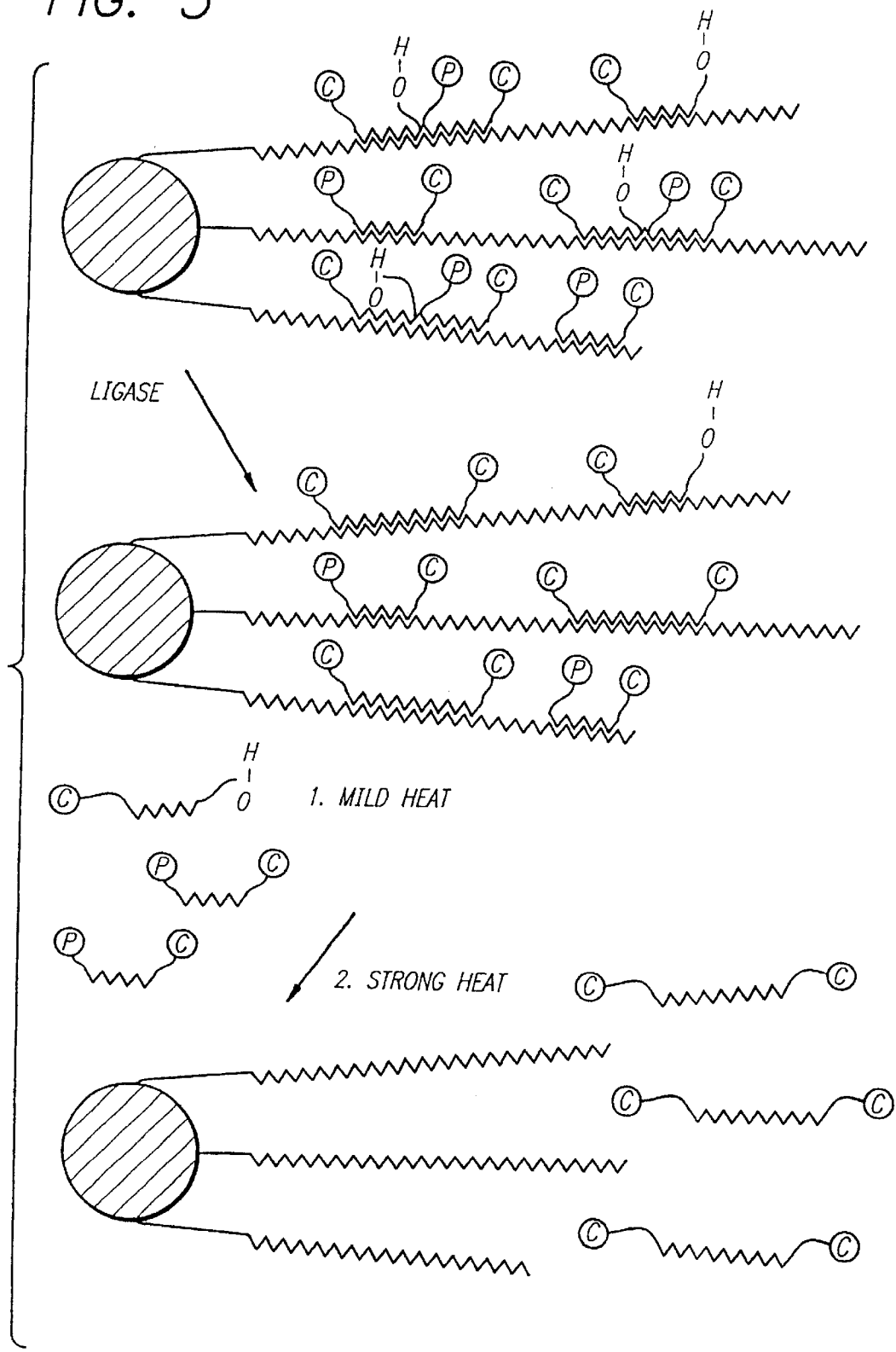
FIG. 5 is a schematic representation of a method of preparation of constant length oligonucleotides using ligase.

METHOD 3
(Ligation, FIG. 5: Preparation of constant length oligonucleotides using ligase.)

This is a variation of Method 2 and is illustrated in FIG. 5. If "n" is a large number, for example, greater than 30, the preparation of a complete mixture of n-mers is impractical. Moreover, if n is large, mismatching between oligonucleotides is problematic. Both of these problems can be avoided by using two complete mixtures of k-mers and m-mers, where k+m=n. In this method, the 3'-end of the k-mers does not contain a free hydroxyl group and the 5'-end of m-mers does not contain a free phosphate. This can be accomplished by using k-mers in which the 3'-end is dideoxy terminated or the hydroxyl group can be phosphorylated or contain a label, such as fluorescein. The 5'-end of the m-mers can have a free hydroxyl group, a label or an active functional group. After hybridization the mixture is ligated. Only two oligonucleotides can be joined together by ligation. Unligated oligonucleotides are removed by increasing the temperature and by washing. If m-mers had a free hydroxyl group at the 5'-end, this hydroxyl group can be now optionally phosphorylated. The new oligonucleotide can now be ligated into a 5'-end. This process can be repeated several times. After dehybridization, there is provided a collection of n-mer oligonucleotides that are complementary to the n-mer oligonucleotides present in the sample.

Figure 6:
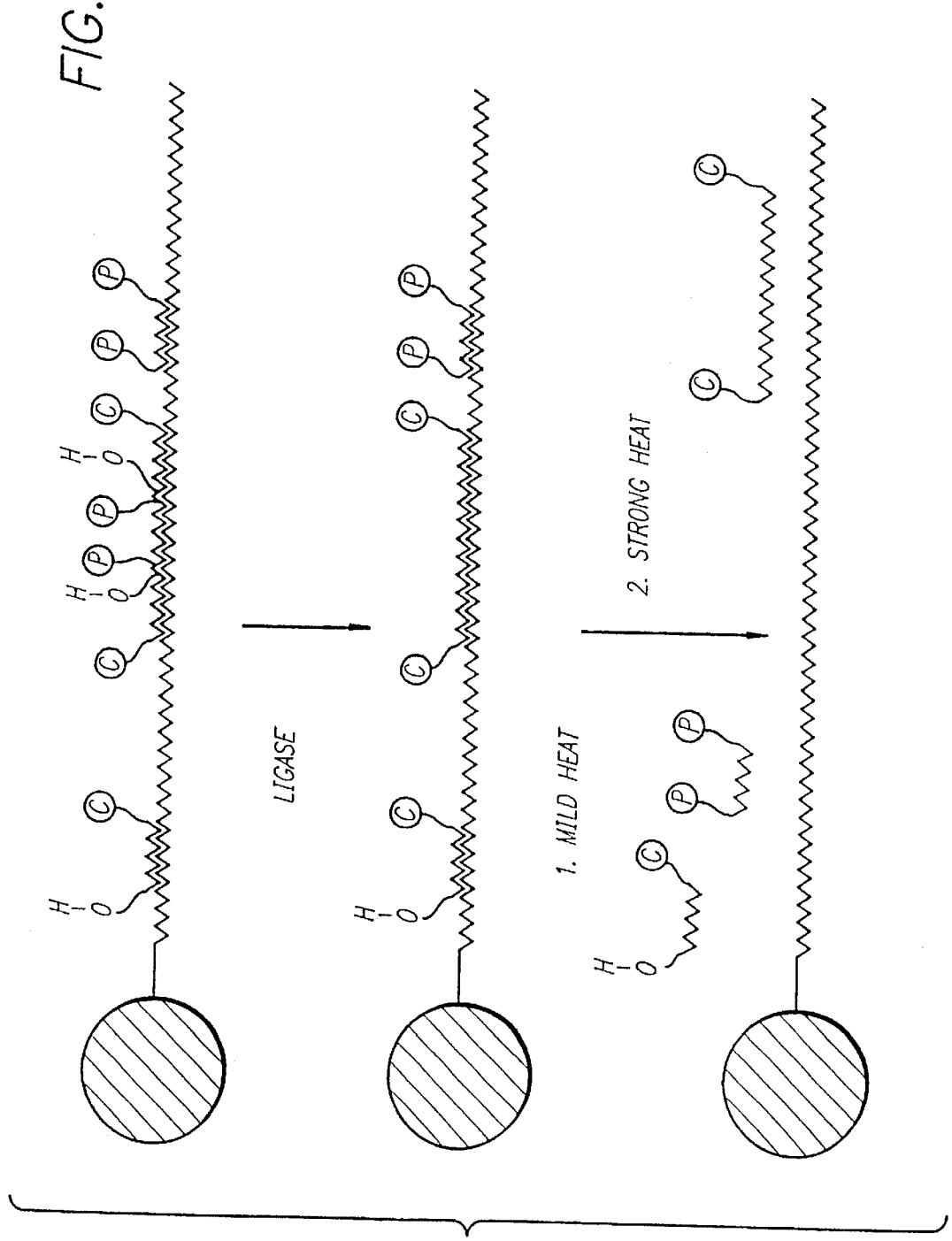
FIG. 6 is a schematic representation of a method of preparing constant length oligonucleotides using chemical ligation or ligase.

METHOD 4
(Chemical ligation, FIG. 6: Preparation of constant length oligonucleotides using chemical ligation.)

Excellent results can be obtained if three sample oligonucleotides, h-mer, k-mer and m-mer, together form an oligonucleotide n-mer after ligation. Chemical ligation is a very efficient method although enzymes can also be used.

As illustrated in FIG. 6, in this case all oligonucleotides are again used as complete mixtures. One series has a phosphate group at both ends, while the other two do not have terminal phosphates at least in the active form. One complete mixture has hydroxyl, amino or thiol groups at the 3'-end, while the other has similar groups at the 5'-end. When these three oligonucleotide types are hybridized and properly located (head to tail) with each other, they are capable of forming a chemical bond with each other. This can be best achieved if the phosphate groups are activated. They can be, for instance, triesters so that two of the esterified groups are pentafluorophenyls or similar good leaving groups. After coupling, the extra pentafluorophenyl can optionally be hydrolyzed away. Upon dehybridization, there is provided a collection of n-mer oligonucleotides that are complementary to the n-mer oligonucleotides that are present in the sample.

TRANSFORMING A LINEAR AMPLIFICATION INTO AN EXPONENTIAL AMPLIFICATION

All four linear amplifications described above and also other analogous linear amplification procedures can be transformed into exponential ones by the method described below.

In linear amplification methods sample oligonucleotides are used as a template set to generate a complementary oligonucleotide set. The process can be repeated several times, but every time about the same number of complementary oligonucleotides is obtained. When these oligonucleotides are pooled, the total number of oligonucleotides is linearly dependent on the number of amplification steps.

In order to transform a linear process into an exponential process, the complementary oligonucleotides obtained in the first step are designed so that they contain a protected thiol, such as thiol acetate, or an aliphatic amino group. After denaturation these oligonucleotides are transferred into a second column that contains a reactive group capable of binding the aliphatic amino or thiol group, such as with a maleimido or isocyanato group. During transfer, a deprotecting reagent, such as hydroxylamine, is added, and the thiol group is exposed. Complementary oligonucleotides will immediately couple with the solid support. Now this support can also be used as a linear amplification template. The amplified oligonucleotide is complementary to the complementary oligonucleotide, i.e., identical to the original sample oligonucleotide, except that it contains a protected aliphatic amino or thiol group. This product is directed to the original column which contains a similar active solid support capable of binding amino or thiol group derivatized oligonucleotides after the protected groups are removed. Now the first column contains twice the original number of oligonucleotides that are identical to the sample. When these are used as amplification templates, twice the original number of complementary oligonucleotides is obtained. After binding these into the second column, that column will contain a threefold number of complementary oligonucleotides as compared to the first cycle. The process can be repeated several times. The amplification after n steps is obtained approximately from the equation:

$$a = 5 * 1.62^{n-4}$$

where a is the amplification coefficient, i.e., how many fold is the increase in the number of oligonucleotides as compared to the original sample. The increase is exponential, but the number does not double in each cycle as it optimally does in PCR. A significant advantage over PCR is that in this procedure the sample and complementary oligonucleotide set are maintained separately. This is highly important when bio-chip arrays are used, because these procedures rely strongly on the hybridization. If every oligonucleotide in the sample has a complementary partner in the mixture, the hybridization with the array will be inefficient.

PREPARING A HIGH DENSITY BIO-COMPACT DISK

In the first step of the actual sequencing, the bio-compact disks (BCDs) are designed to recognize all 16-mers in the sample. This is achieved by $(8,\{0\},8)$-recognition, i.e., the spacer has two 8-mer side-arms and no soluble probe oligonucleotides are used. This recognition will be denoted also as $(8,8)$ recognition. There are about $64*10^3$ different 8-mers and $4.3*10^9$ different pairs of two 8-mers (Table 4). A certain area containing one gold sphere is called a biobit. The area of each biobit is about 100 $\mu m^2$. This area is covered by thousands of spacers having similar $(8,8)$-pairs of oligonucleotides as side-arms. Each biobit should contain only one type of a $(8,8)$-pair of oligonucleotides and there must be at least one biobit for each of the possible different 8-mer pairs. Presently available CD-ROM readers are able to read $0.6*10^9$ bits from one compact disk (CD). Thus, about eight BCDs are needed for all possible 8-mer combinations. The density of CDs can be increased many times, potentially 20-fold, when blue semiconductor lasers are used instead of IR-lasers. This will be reflected nearly linearly in increased performance of BCDs.

Figure 7:
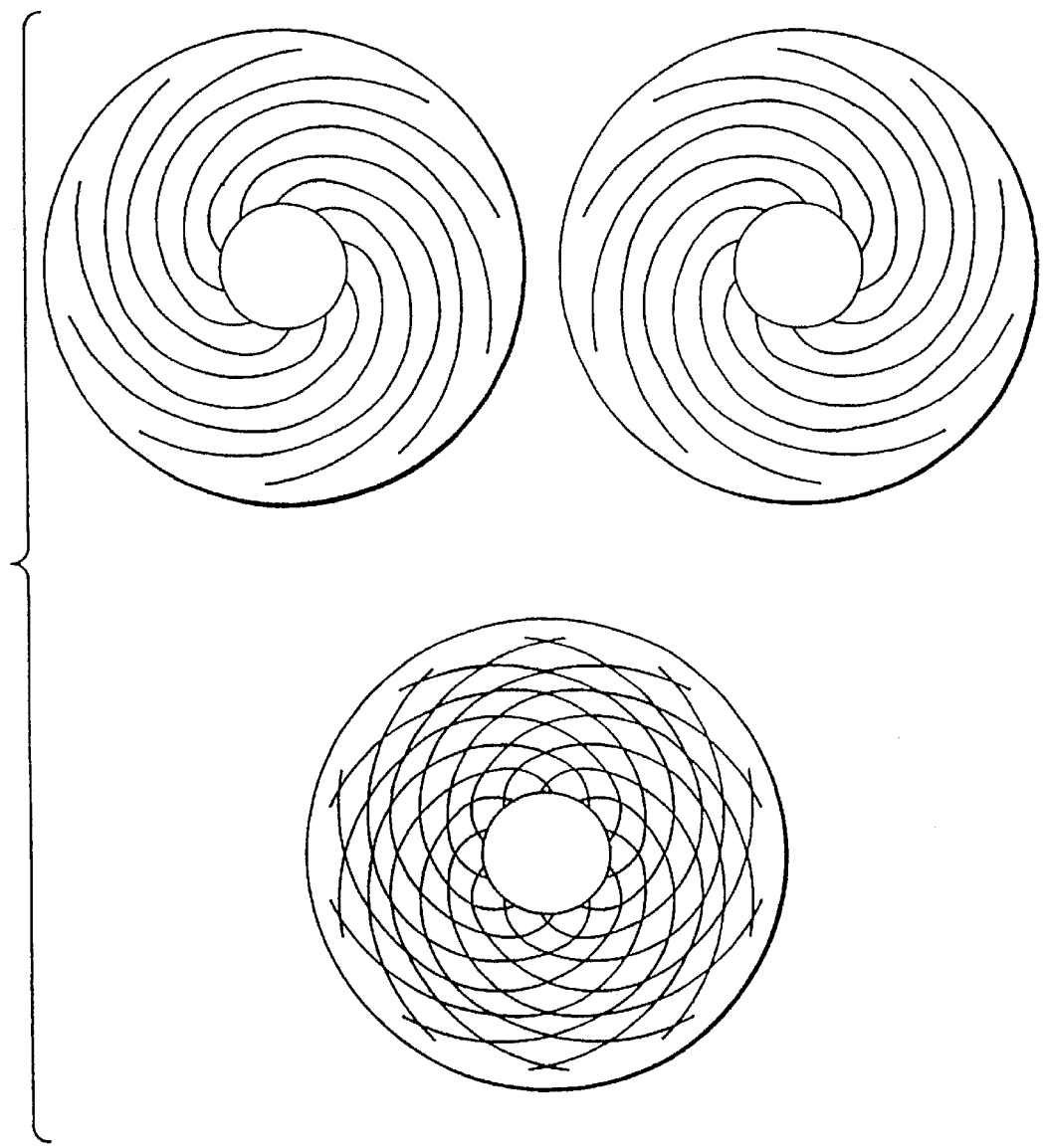
FIG. 7 is a schematic representation of two complementary stamps used in the preparation of bio-compact disks having oligonucleotides attached to their surface.

A complementary printing method described here can be used to fabricate complicated high resolution patterns in one printing step once a complementary stamp has been created (FIG. 7). Photolithographic methods or comparable high resolution patterning methods are needed to make the complementary stamp. All lower side-arm oligonucleotides can be printed in one step using one complementary stamp. Similarly all upper side-arm oligonucleotides can be printed in one step. Thus, two stamps are needed to fabricate one BCD. Because eight different BCDs must be produced, the total amount of different stamps is 16.

FABRICATING A COMPLEMENTARY STAMP

One complementary stamp can be used thousands of times. However, fabricating one complementary stamp can require tens of photolithographic or printing steps. Printing methods in this application have a fundamental advantage over lithographic methods in that the oligonucleotides can be purified before attaching them onto the surface.

The fabrication of complementary stamps which can be used in the (8,8)- and (8,{11},8)-recognition strategy described herein. Altogether four different pairs of complementary stamps must be produced, each pair is chemically identical, i.e., they contain the same 16,384 oligonucleotides (8-mers), but the spiral channels go in opposite directions (FIG. 7). Because there are 65,536 different 8-mer oligonucleotides, four stamps are needed to contain a complete, set (4×16,384=65,536). All 16 possible combinations of clockwise and counter-clockwise spiral stamps give all 4.3 billion different 16-mer oligonucleotides constructed as pairs of all possible 8-mer oligonucleotides (Table 4).

First, the spiral channels (16,384) are printed onto soft polycarbonate. Each channel is about 4 μm wide and 1–2 μm deep. This is similar to printing compact disks, in which case micrometer resolution is standard. It is preferable to have hydrophobic ridges, while channels are hydrophilic, in the finished stamp. The ridges are also 4 μm wide. For this purpose the disk is coated with a resist and the same stamp that was used to print spiral channels is used again to expose the bottoms of the channels. Oxygen etching is used to remove any residual resist from the channels. The surface is coated with amino groups by ammonia plasma. The resist layer is removed from the ridges. Polyethylene glycol spacers having, for instance, isothiocyanato groups on both ends are attached to the amino groups. Using an excess of spacers only one end will bind with the surface and the other can be used to bind oligonucleotides having an additional aliphatic amino group.

The spiral channels (16,384) are preferably in 256 groups of 64 channels (256×64=16,384). These groups are separated so that an ink-jet or equivalent method can be used to cover one group with a certain 4-mer oligonucleotide having an aliphatic amino group. Thus, a known 4-mer oligonucleotide is in 64 different nearby channels. Each of the 256 possible 4-mers occurs in one of the 256 channel groups once and only once. The next step is to deposit 64 different 4-mer oligonucleotides separately into each of 64 channels in one group and bind it chemically with the first 4-mer oligonucleotide. On one disk, all of these second 4-mer oligonucleotides can have the same terminal nucleotide, for example, A. After four chemically different disks are fabricated, all oligonucleotides (A, C, G and T) appear at terminal positions on one disk. Because there are 256 different groups, each of the second 4-mer oligonucleotides will appear 256 times on the same disk. The second 4-mer oligonucleotides can be printed onto all these locations simultaneously. To avoid contamination, each oligonucleotide should be printed with a dedicated stamp. All stamps look exactly similar. They have 256 equally spaced (about 0.6 mm) spiral channels. One spiral channel is 5–8 μm wide. Channels can be hydrophilic, while the area between is hydrophobic. After wetting with oligonucleotide solution, only the channels retain the solution, which is partially transferred after the contact with the substrate. Another method is to etch hydrophilic cavities into the bottom of the channels, which in this case are hydrophobic (FIG. 10). Preferably these cavities are coated with latex spheres, which are porous, hydrophilic and elastic (FIG. 11). The channel itself is hydrophobic, so that all solution is retained in the spheres. This gives better control of the amount of the solution and the location of the solution both in the stamp and on the substrate. The spheres are chemically bonded onto the stamp using conventional binding chemistry in a manner suitable for latex spheres, for example, using an amide bond between the spacer and the latex sphere. Optionally the latex sphere is located in a dent on the stamp to get stronger binding.

Also, oligonucleotide analogs can be substituted for the oligonucleotides above. This is especially applicable in the complementary stamp, because some oligonucleotide analogs are easier to couple in water solution than oligonucleotides. For instance, using water soluble carbodiimide, 4-mers containing an amino group can be coupled with another 4-mer containing a carboxylic group. Moreover, some oligonucleotide analogs give stronger hybridization than oligonucleotides themselves and are useful in the complementary stamp and in the final oligonucleotide array.

FABRICATING A BIO-COMPACT DISK

Figure 8:
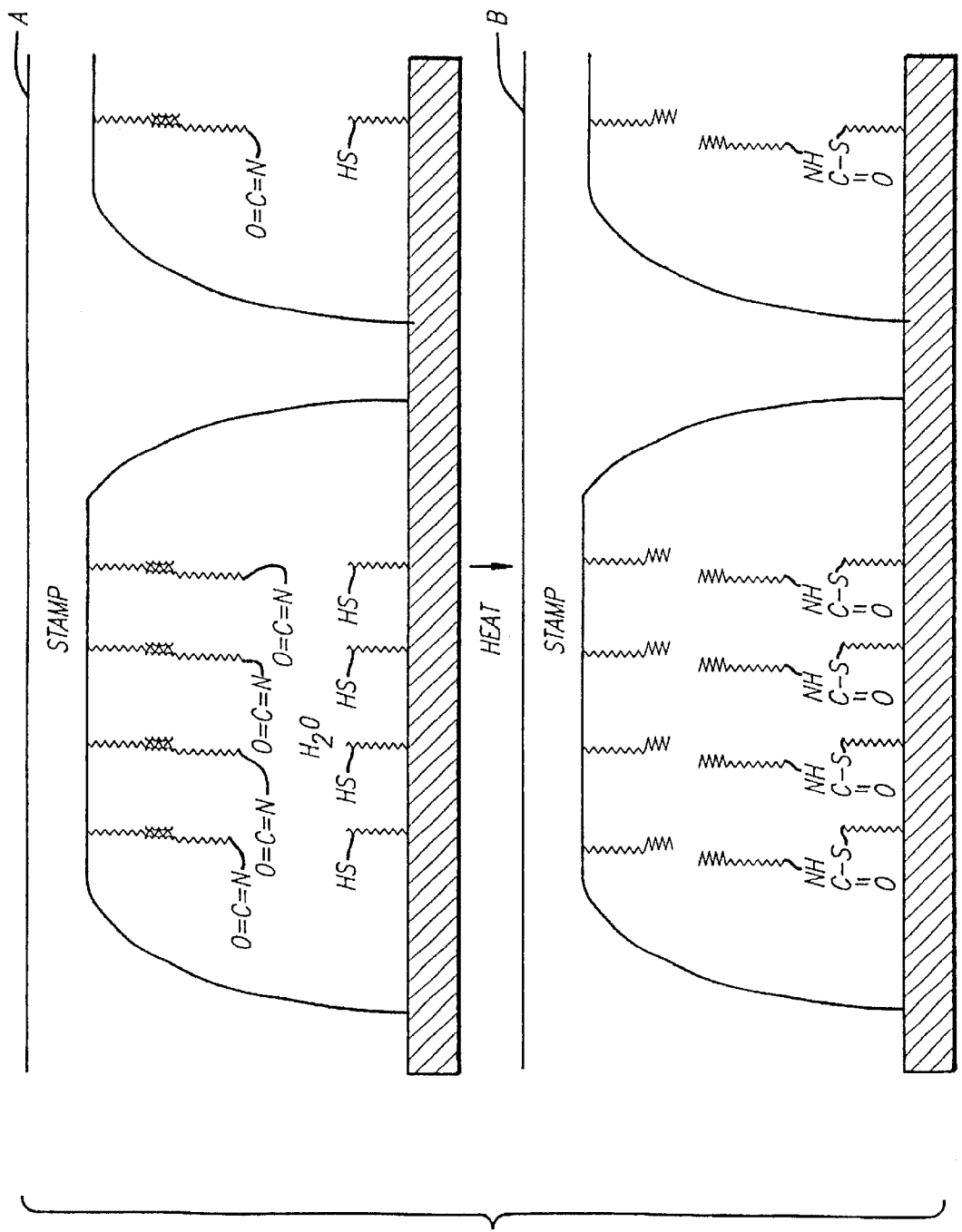
FIG. 8 is a schematic representation of one embodiment of using the stamps of FIG. 7 for printing where the stationary oligonucleotides to be attached to the solid are on the walls of a grove formed in the stamp.

In the following description it is assumed that all stamps have already been made. At first lower side-arm oligonucleotides are printed. A complete mixture of 8-mers is prepared. The synthesis is performed so that the 3'-end of the oligonucleotides is connected with a polyethyleneglycol (PEG) spacer, which has a thiol group in the other end. (Alternatively the thiol group can be in the stationary spacer on the substrate and isocyano or maleimido group can be on the PEG spacer). The solution of the complete mixture is used as an ink to wet a stamp (FIG. 7, upper left corner). In one configuration of the stamp, the stationary oligonucleotides are on the walls of a groove that is 1 μm deep (FIG. 8: Concave complementary printing). After hybridization the excess of oligonucleotides is washed away. The wet stamp is pressed firmly against the BCD, which has maleimido groups at the lower part of the spacer. The thiol groups will couple very fast with the maleimido groups. Because of the relatively long distance, only a few couplings may take place at this stage. To release the oligonucleotides and to drive the reaction into completion, the thin water layer is heated by microwaves or by infrared radiation for about one minute. The oligonucleotides are released from the stamp and are then free to diffuse. An oligonucleotide can diffuse 1 μm in one second and 8 μm in one minute. Due to an excess of the maleimido groups, all thiol derivatized oligonucleotides will be bound efficiently. The printing step is completed and the stamp can be removed. The cleavable spacer molecules now have a complete lower side-arm. The protective group is removed from the upper side-arm location and the printing step is now repeated to insert the upper side-arm oligonucleotides (FIG. 7. Stamp in upper right corner). In this case the 5'-end of the oligonucleotide is connected with the polyethyleneglycol spacer. After washing and drying the BCD is ready for use.

SEQUENCING STRATEGY

Instead of trying to sequence the whole genome at one time, chromosomes may be separated, and the two strands of each chromosome may be separated. Only one strand of each chromosome needs to be sequenced; the sequencing of the other one is optional and serves as a double check. For sequencing purposes it is important to know what is the probability for an n-mer that is already known to be in the chromosome to occur a second time. The longer the characterized oligonucleotide, the smaller the probability it will occur twice. In order to achieve reliable sequencing, this probability should be so small that characterized oligonucleotides occur only once in the chromosome, i.e., this probability should be smaller than $4*10^{-9}$. Close inspection of the Table 2B reveals that for 28-mers this probability is below the required limit ($1.7*10^{-9}$). For 24-mers the corresponding probability is $4.4*10^{-7}$, which indicates that about one hundred 24-mers can occur twice in the chromosome. Thus, knowing 28-mers guarantees unique sequencing, while shorter oligonucleotides might lead to ambiguities.

There are about $65*10^{15}$ different 28-mers. An array containing all these oligonucleotides would have an area of 130 acres provided that one oligonucleotide occupies only 10 $\mu m^2$. This kind of array is clearly impractical to manufacture, process and read. On the other hand, Table 4 indicates that all 14-mer biobits can fit onto a single BCD (BCD area=$4.2*10^4$ mm$^2$). Thus (7,7)-recognition would be desirable from a purely practical point of view. As is seen from Table 2A, a given 14-mer is not found at all with the probability of 0.393 and can be found twice and three times with the probabilities of 0.173 and 0.050, respectively. Because of the occurrence of repetitive sequences, these probabilities are higher and correspondingly the number of different 14-mers is lower; and less than half of all possible 14-mers are likely to be found in a chromosome. However, this is much too high a probability for useful sequencing and 14-mers are too short to be useful in the sequencing of the whole chromosome at one time.

Figure 9:
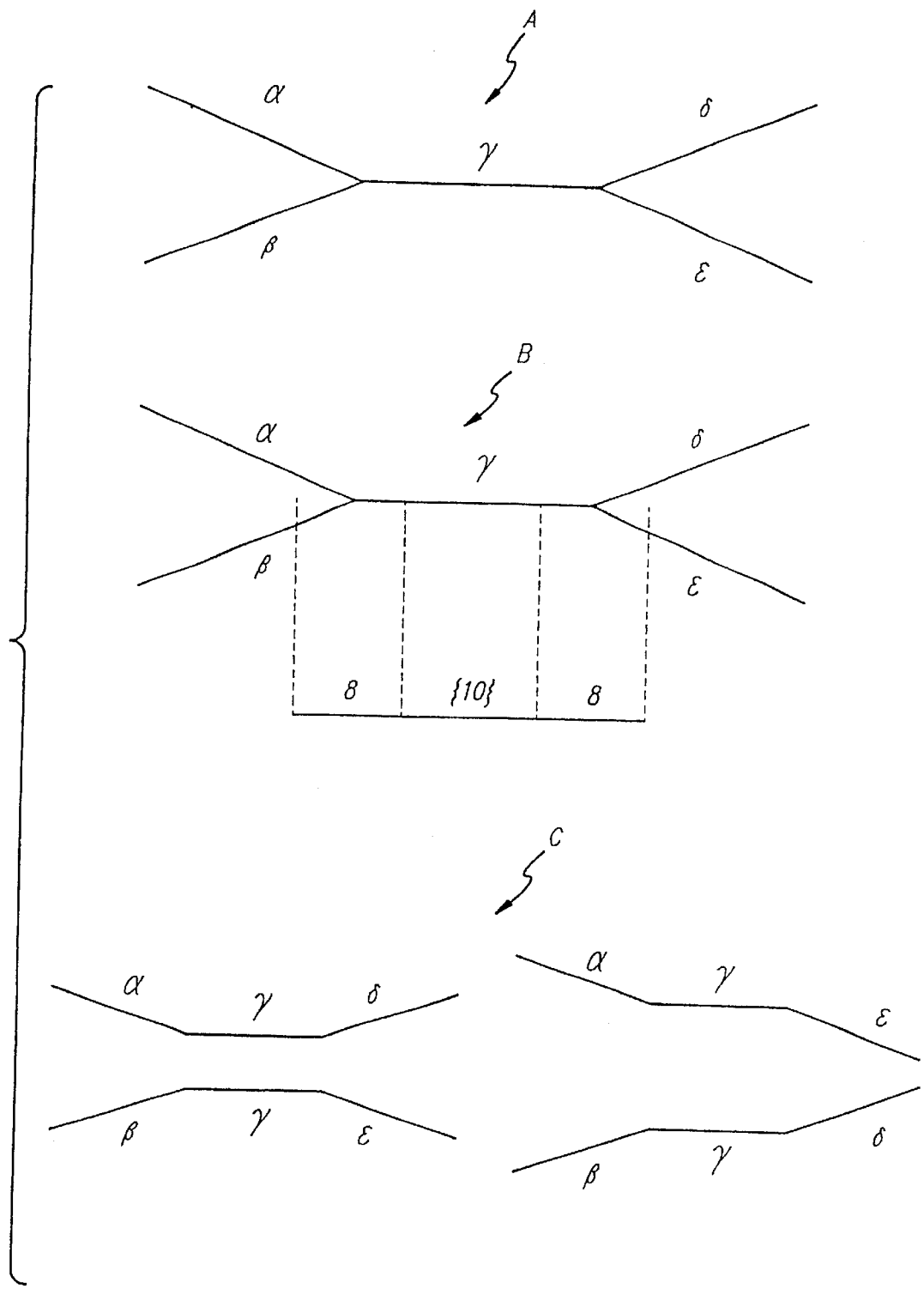
FIG. 9 is a schematic representation of the use of selective recognition, (8,{10},8)-recognition, to determine sequences around 16-mers occurring twice in a chromosome.

16-mers may be the shortest oligonucleotides that give enough information for de novo sequencing and are still within practical limit of BCDs. The sequencing strategy is based on the use of the BCDs that are prepared as described above. The (8,{0},8)-recognition is used first. This gives information about all 16-mers that are part of the chromosome. A 16-mer that is already once in a chromosome can occur with a probability of 0.028 also a second time. Taking into account the size of the chromosome, this probability indicates that up to one million 16-mers can occur twice in a chromosome. Each of these leads to a branching point in the sequence information. This is depicted in FIG. 9, where α and β denote arriving sequences and δ and ε denote leaving sequences from a certain 16-bp sequence γ. Identical branching occurs at some other point in the sequence obtained this way. If all branching points are drawn, a network pattern rather than a sequence is obtained. Possible sequences over these branching points can be denoted α-γ-δ or α-γ-ε and β-γ-δ or β-γ-ε (FIG. 9). Only two of these possibilities are in the real chromosome. The sequence γ occurs, of course, in both of them, while each of the other sequences α,β,δ, or, ε occurs only once. Thus, it is sufficient to find out if the sequence α-ε-δ or α-ε-ε is in a particular chromosome. Immediately it can be deduced which of the others is also in this chromosome. The method that is used will find out both simultaneously so that the other can be used as a double check.

The total length of stationary oligonucleotides should be 26–28 nucleotides in order to get a unique sequence without branching points. Because this is practically impossible, other strategies must be used. One possibility is to use (8,{11},8) recognition as an alternative, where {11} denotes a complete mixture of 11-mers. The sample is prepared as earlier except that 27-mers are the target length. The sample oligonucleotides are applied onto the similar set of the BCDs as was used earlier. After hybridization a complete mixture of 11-mers is added. In some cases there is a just sufficient space left for an 11-mer to also hybridize. After ligation all other ones are removed by mild heating and washing. It will not known which 11-mer used this space, but both terminal 8-mers will be known. In FIG. 9 is shown only one possible hybridization. All possible hybridizations, i.e. shifted by ±1,±2,±3, etc. nucleotides, are observed. The combination of these 8-mers carries enough information to deduce the sequence almost in unequivocal way (FIG. 9B).

(8,{11},8)-Recognition is substantially equivalent to the compete recognition of 27-mers. Although only 16 nucleotides are recognized by each assay element, i.e., each particular spacer molecule having 8-mer sidearms, this recognition pattern provides more information than recognizing 16-mer strands of the DNA. This is illustrated in FIGS. 12 and 13, where for simplicity, a comparison (4,4)- and (4,{5},4)-recognition is used as an example. If a certain 8-mer sequence occurs twice in the DNA, e.g., $A_8$ of FIG. 12, two alternative overall sequences are possible. However, in an analogous case, ($A_4+A_4$) as illustrated in FIG. 13, (4,{5},4)-recognition provides an unambiguous result. This is because the subsequences preceding and following the degeneracy contain common information (underlined in FIG. 13), i.e., the TATT sequence and the GTGG sequence, respectively. Accordingly, in a similar manner, one could use (8,{11},8)-recognition for sequencing a 27-mer segment without the use of (8,8)-recognition, although concomitant use of both is preferable to obtain the most certain results possible.

In practice, several bio-compact disks are used for the complete sequencing of the genome. In a preferred embodiment, the spacer molecules are formed with two 8-mer oligonucleotide sidearms, one between each of the two ends of the spacer molecule and the cleavage site. All possible sequences of the 8-mer oligonucleotides are represented in the sidearms. The location of each of the possible 8-mer pair of sequences attached to the spacer molecules on the surface is determined in the manufacturing process so that the presence or absence of any particular sequence can be detected. In practice, each disk may contain known subsets of all possible sequences in order to have a bio-compact disk of reasonable size that can be utilized with commonly available instrumentation. Prior to contacting the assay element, i.e., the surface having the above-described spacer molecules attached at the predetermined locations, a mixture of soluble 11-mer oligonucleotides having all possible sequences is added to the sample to be tested, and the resultant solution is applied to the surface of the bio-compact disks. Respective sequences of the sample oligonucleotide fragment bind to complementary sequences on the spacer molecules and the bound segments are ligated. The respective sequences are then determined as has been described previously. For economy and time efficiencies, the foregoing method can be repeated in parallel for all 27-mer segments. The collection of information from the 27-mer segments is then utilized to determine the entire sequence of the genome by known methods. While the above description is directed to the use of $(8,\{11\},8)$-mer recognition, the method is applicable to $(p,\{q\},r)$-mer recognition in general, wherein where p, q and r are integers selected from the integers 4–10,000, most advantageously 6–26 and (p+q+r) does not exceed 30,000, most advantageously 60. It is generally preferred that p=r and q>p. Because the soluble oligonucleotide probe (q) should be so strongly bound that it is not detached from the sample oligonucleotide during hybridization with stationary probes (p and r), it is required that q>p. This may also be accomplished by using some soluble oligonucleotide analogs, such as peptide oligonucleotides, which hybridize very strongly. To achieve a constant temperature hybridization p and r should be equal. However, for the same reason the oligonucleotide probes containing very little cytidine or guanidine should be made longer to get stronger binding.

For small genomes and for sequencing individual human genes or groups of genes p=r=7, and q=9 is adequate. In this case one disk is enough for the sequencing.

To measure repeat sequences that comprise a large part of the human genome, p, q and r may be very large, about 100–10,000. Centrifugal or electromagnetic force may be used to measure the binding strength. Ligation may be used optionally to check the presence or absence of gaps in the double helix.

Gene expression levels may be measured by this system. Often it is preferable to use very large fragments for recognition. This saves space. Mismatching is not a serious problem in the study of gene expression and thus, use of smaller probe oligonucleotides does not provide a great advantage.

FRACTIONATION OF THE SAMPLE

The sample containing oligonucleotide fragments may be applied directly onto the surface of the BCD. However, it is preferable that the sample is fractionated at least into certain subclasses. A given subclass may be localized onto a certain area on the BCD surface increasing the probability of the hybridization and decreasing the probability of mismatch, if the fractionation and the BCD patterning are designed properly.

Mismatching is one of the worst problems in the use of oligonucleotide arrays. Mismatching is most frequent between oligonucleotides that differ only in one nucleotide. Despite this, many oligonucleotide arrays are fabricated so that neighboring oligonucleotide sites differ only by one nucleotide. The following procedure allows the fabrication of the arrays and fractionation systems that contain an oligonucleotide subclass in which all oligonucleotides are different in at least two base pairs. This procedure may be extended to create a sub-array, where each oligonucleotide has at least three different nucleotides when compared with any other oligonucleotide in that sub-array.

To guarantee that in a certain subclass of oligonucleotide n-mers each oligonucleotide differs from any other by at least two nucleotides, this subclass should be constructed by choosing n/2 quartets of dimeric oligonucleotides from Table 5. It is supposed that n is divisible by 2. As an example, a subclass of tetrameric oligonucleotides (n=4) is generated by choosing two (4/2=2) quartets of dimers, for example, quartets 1 and 3. Sixteen tetrameric oligonucleotides may be generated by combining one dimer from quartet 1 with another dimer from quartet 3. These sixteen tetramers are shown in Table 6. The tetramers in one row differ by two nucleotides, as do the tetramers in one column. Two tetramers taken from two different rows and columns differ by four nucleotides. All together sixteen subclasses of tetrameric oligonucleotides may be generated by using Table 5. Each subclass contains sixteen oligonucleotides and thus, all 256 (16×16=256) tetrameric oligonucleotides will be generated and each is a member of one and only one subclass. Similarly, all oligonucleotide n-mers (where n is even) may be divided into subclasses. The number of subclasses is $4^{n/2}$ and each contains e oligonucleotides, i.e., the total is $4^n$ as it should be.

The construction of oligonucleotide n-mers from dimers is only conceptual and is no limitation on the actual synthesis that may be performed using monomeric, dimeric, etc. nucleotide derivatives as is described elsewhere. However, dimers provide the most practical way for the synthesis of the arrays designed using Table 5.

The sequencing is performed advantageously by using (8,8)-, or $(8,\{11\},8)$-recognition or the combination of these. The sample oligonucleotides may be first fractionated into $4^4$ (256) subclasses based on the 8-meric sequence in the 3'-end of each oligonucleotide. Each of these subclasses is further fractionated into 256 subclasses base on the 5'-end of each oligonucleotide. Thus, altogether $4^8$ (65,536) subclasses are obtained. Each of these subclasses contains $4^8$ (8,8)-oligonucleotide pairs. One subclass will cover about 0.25 mm×0.25 mm on the BCD.

In order to get $4^8$ subclasses on their proper sites on the disk the sample must be fractionated. This task can also be performed by a closed BCD (Disklab) as is described in the following for the (4,4)-recognition case. Short oligonucleotides are used as an example to simplify figures. Now both the first and second recognition oligonucleotides can be divided into $4^2$ (=16) subclasses, i.e., there are 16×16 (=256) combinations. This example can be generalized in an obvious way to longer oligonucleotides.

Figure 14A:
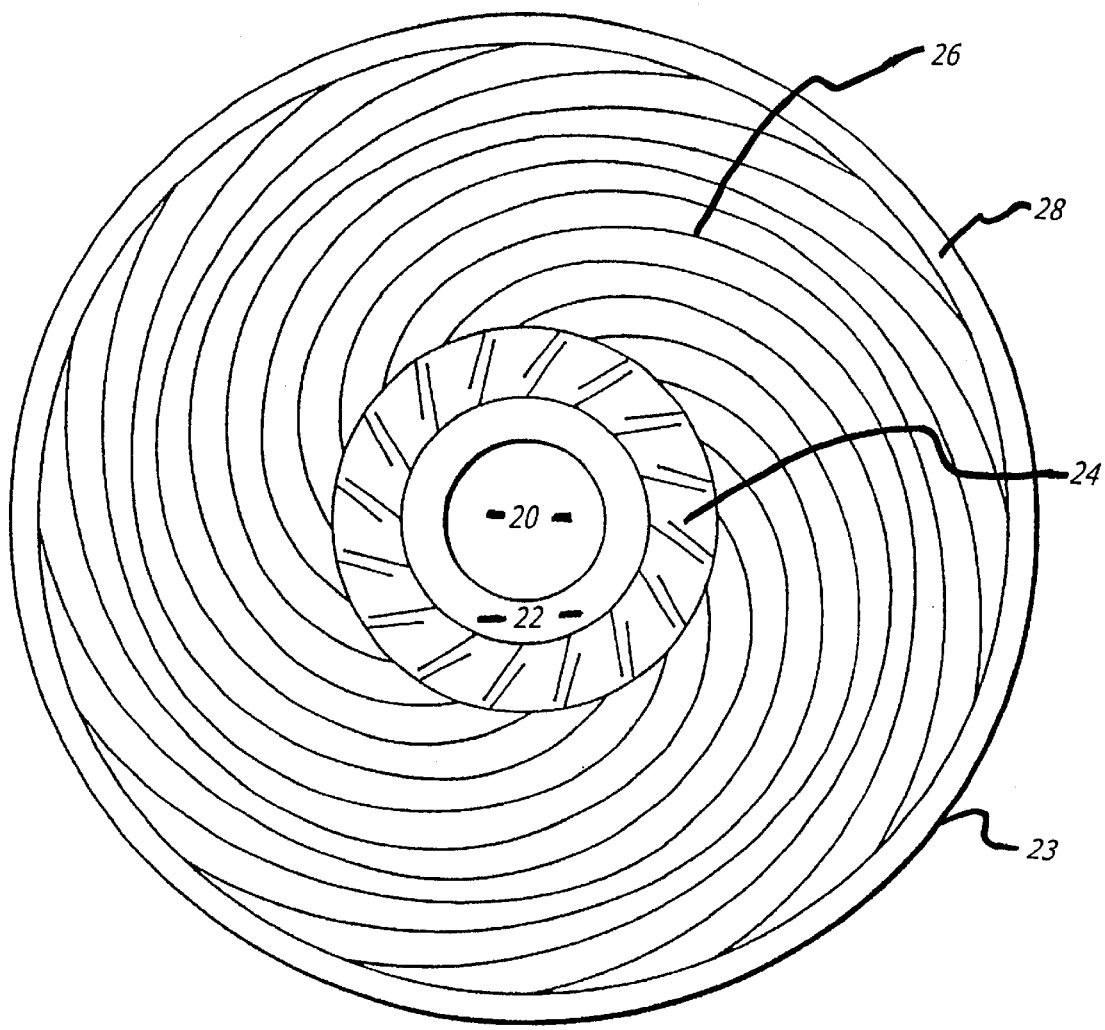
FIG. 14A is a schematic representation of a fractionation disk. The first fractionation may be performed in the central sixteen compartment area. The fractions may be further fractionated in the spiral channels or capillaries.

The fractionation disk 21 consists of two separate disks 23, 25 which are clamped together so that they can be detached when needed. The overall structure of the other half is depicted in FIG. 14A. The structure of the disk is described starting from inside and moving outward. The smallest circle in the center is a hole 20 that is optional for handling and rotating. The unstructured area 22 between two circles is a container for an elution buffer. The area 24 that is divided into sixteen compartments by partial double walls is a circular fractionation 'column'. The first fractionation is performed in this part. The sixteen spiral channels 26 may be used in the second fractionation step. Finally, the unstructured outer perimeter 28 is used to collect waste.

Figure 14B:
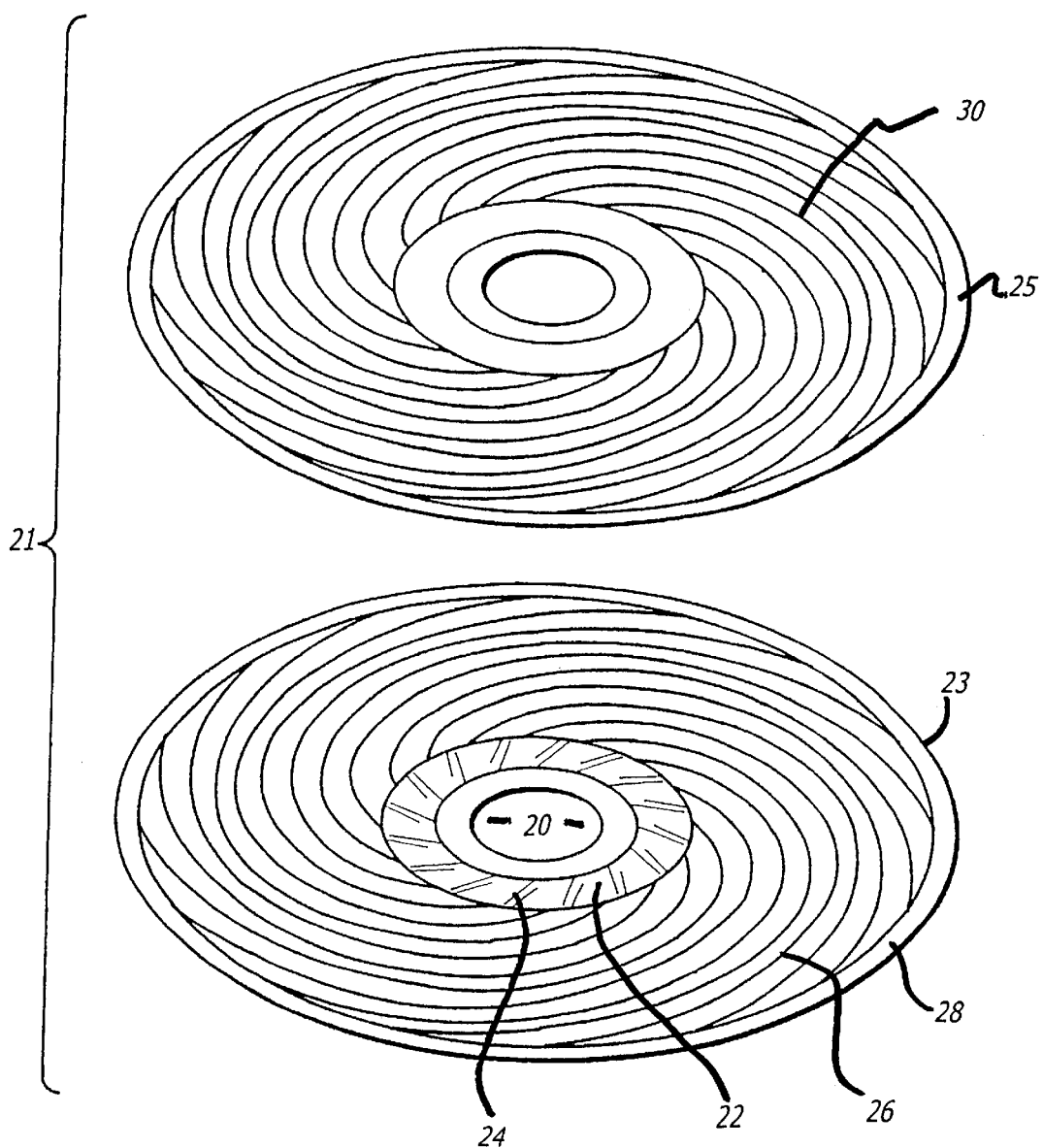
FIG. 14B demonstrates that further fractionations may be performed after another disk is attached onto the disk depicted in FIG. 14A.
Figure 14C:
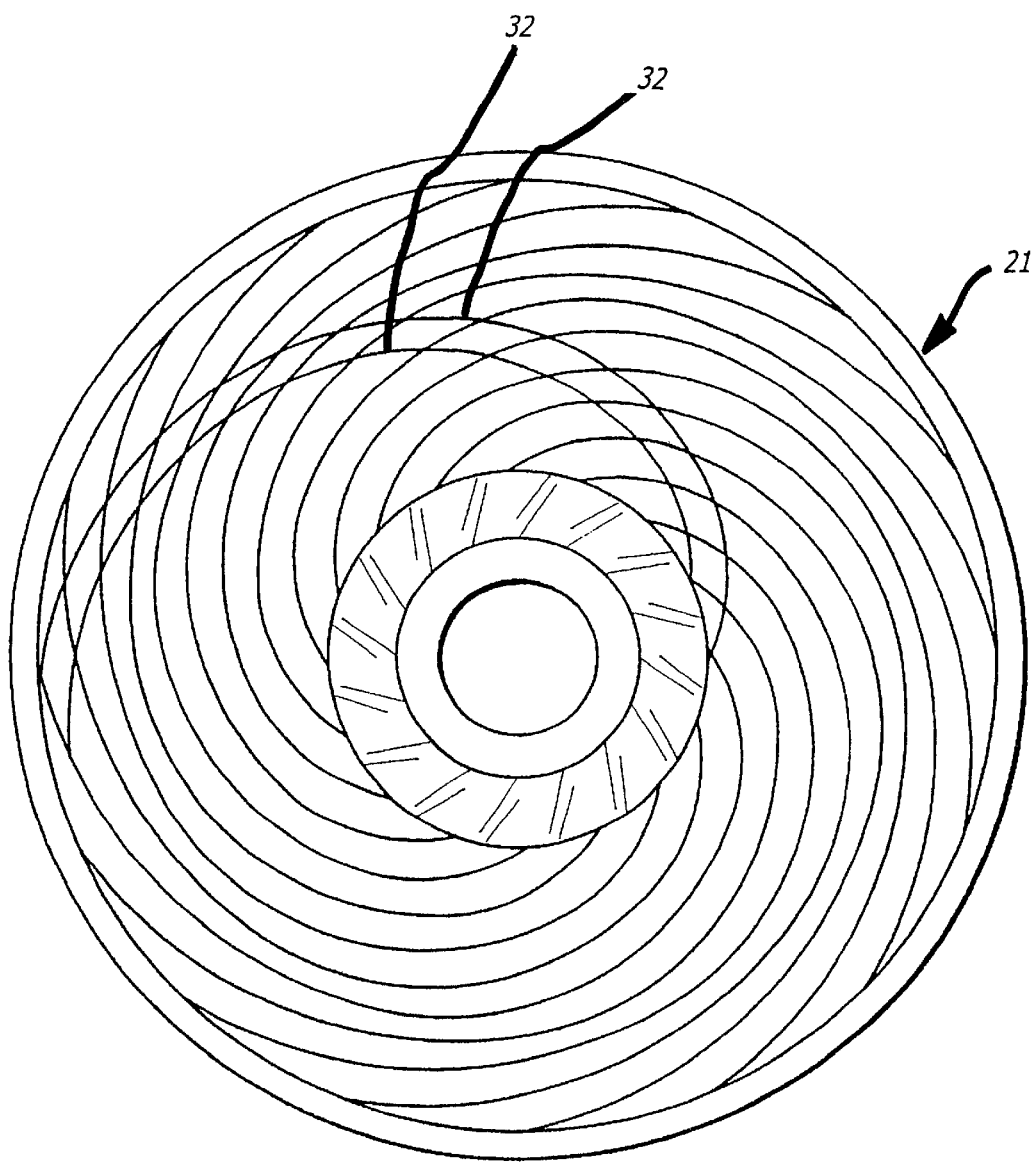
FIG. 14C represents a top view of intersections of capillaries and one oligonucleotide class zone.

On top of the first disk 23 is placed a second disk 25 (FIG. 14B) that is coated with sixteen oligonucleotide subclasses so that they form the spiralline counterclockwise pattern 30. This disk 25 is called a collector disk. The collector disk may be flat or mechanically patterned. In any case the channels in the first disk must be sealed so that the eluting buffer and DNA fragments are not exchanged between covered channels, which are more appropriately called capillaries, when two disks are clamped together. FIG. 14C depicts a top view of the operational disk 21. Only two subclass zone 32 are shown to provide clarity. These zones 32 as do all other fifteen zones intersects all sixteen capillaries. Altogether there are 256 intersections in this embodiment of the invention.

Figure 15:
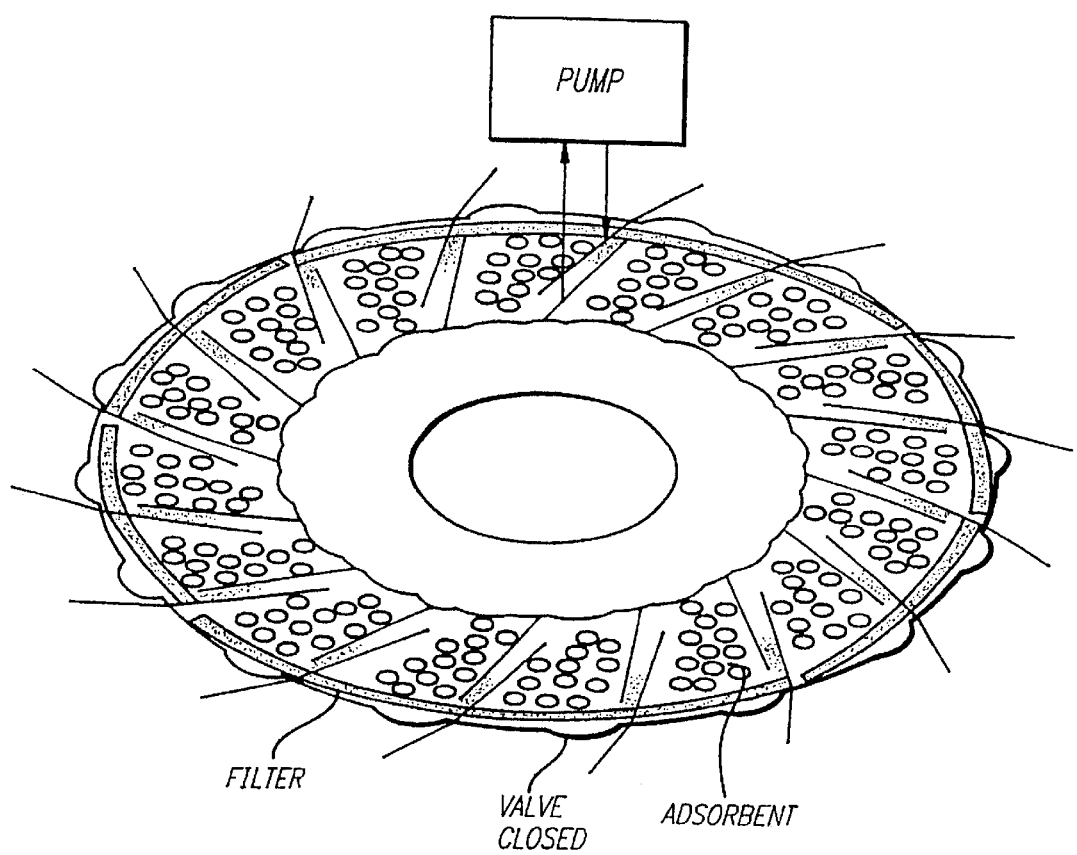
FIG. 15 is a schematic representation of a central fractionation area. The sample may be circulated around this area which, in this particular embodiment contains sixteen compartments. Each compartment contains a specific oligonucleotide subclass probes.
Figure 16:
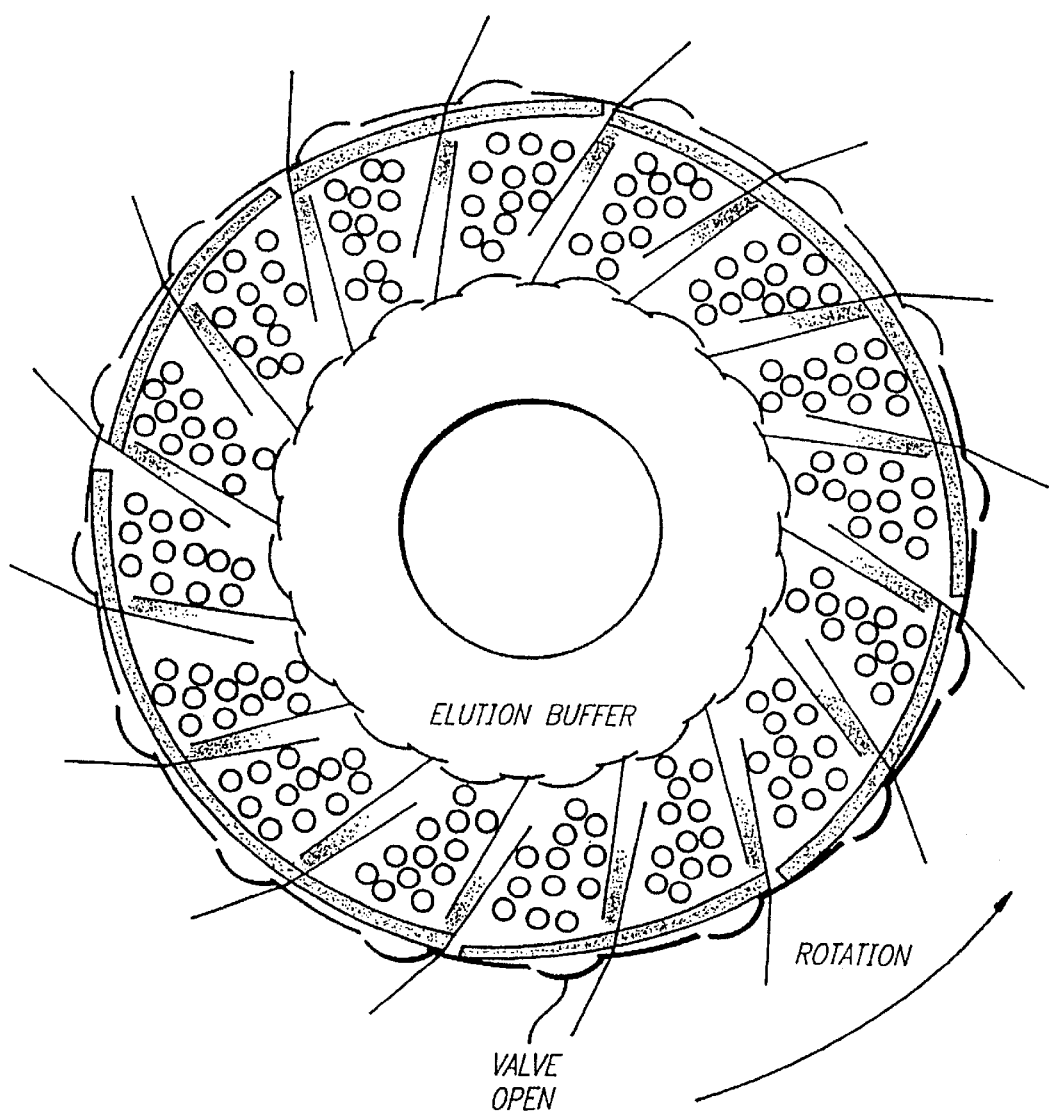
FIG. 16 illustrates that the oligonucleotides may be eluted into the capillaries by spinning the disk after denaturation.

The central part of the disk that contains the circular first fractionation zone is depicted in more detail in FIG. 15. Each of the sixteen chambers contains loosely packed solid support coated with certain subclass of 8-meric oligonucleotides. One 4-meric end, for example 3'-end, of these oligonucleotides is formed according to Table 5. The other 4-meric end (5'-end) contains all possible 4-meric combinations. Each of the sixteen 4-meric 3'-end subclasses occurs in one and only in one chamber. The sample is circulated in an optimal temperature by pumping. The pump may be external or internal. After an equilibrium is reached, the unbound sample is removed and the solid support is washed to remove unbound and loosely bound oligonucleotides. The disk is heated, for example, by IR-radiation to denature the hybridized oligonucleotides, and rotated very fast, for example 200–50,000 rpm, so that the valves are opened due to centrifugal force. The fractionation unit can also be a module that can be rotated relative to the rest of the disk so that all 32 valves will open simultaneously. In this case the valves can be simply holes that are covered in one position and are open in another position. Elution buffer will carry the denatured oligonucleotides into the capillaries each of which have sixteen 8-meric oligonucleotide subclasses zone-wise in their one wall. In this case each 8-meric subclass is completely formed according to the Table 5. Thus, each of the sixteen fractions will be further divided into sixteen fractions. These all fraction may be attached with the collector disk that is separated from the other disk.

The collector disk is placed on top of the sequencing disk that is patterned analogously. The resolution in the sequencing disk is generally, but not necessarily, much higher than in the collector disk.

The purpose of this fractionation method is to concentrate right kind of sequences close to their complementary probe oligonucleotides. Using constant length oligonucleotides this fractionation is further improved. In any case this method vastly increases the concentration of the right kind of oligonucleotides where they can be detected.

While this invention has been described with respect to some specific embodiments, it is understood that modifications thereto and equivalents and variations thereof will be apparent to one skilled in the art and are intended to be and are included within the scope of the claims appended hereto.

TABLE 1

|  | Weight of all n-mers (mg) | Average no. of copies of each oligonucleotide in 10 mg |
|---|---|---|
| 16-mers | $34.3 * 10^{-9}$ | $3 * 10^8$ |
| 24-mers | $33.2 * 10^{-4}$ | $3 * 10^3$ |
| 26-mers | $57 * 10^{-3}$ | 180 |
| 28-mers | 0.86 | 11 |
| 31-mers | 71.3 | |

TABLE 2A

The probability of not finding at all or finding once, twice or three times a given n-mer (n = 14, 16, 17, 18 or 19) in a chromosome.

|  | 14-mer | 16-mer | 17-mer | 18-mer | 19-mer |
|---|---|---|---|---|---|
| p(0) | 0.393 | 0.943 | 0.986 | 0.996 | 0.999 |
| p(1) | 0.366 | $5.5 * 10^{-2}$ | $1.4 * 10^{-2}$ | $3.6 * 10^{-3}$ | $9.1 * 10^{-4}$ |
| p(2) | 0.173 | $1.6 * 10^{-3}$ | $1.0 * 10^{-4}$ | $6.6 * 10^{-6}$ | $4.1 * 10^{-7}$ |
| p(3) | 0.050 | $3.1 * 10^{-5}$ | $5.1 * 10^{-7}$ | $8.0 * 10^{-9}$ | $1.3 * 10^{-10}$ |
| p(2,3) | 0.397 | $2.8 * 10^{-2}$ | $7.3 * 10^{-3}$ | $1.8 * 10^{-3}$ | $4.6 * 10^{-4}$ |
| p(1,3) | | | | | |
| Total no. of oligonucleotides having freq. >1 | $60 * 10^6$ | $7.0 * 10^6$ | $1.8 * 10^6$ | $0.45 * 10^6$ | $0.11 * 10^6$ |

TABLE 2B

The probability of finding once, twice or three times a given n-mer (n = 20, 21, 22, 24 or 28) in a chromosome.

|  | 20-mer | 21-mer | 22-mer | 24-mer | 28-mer |
|---|---|---|---|---|---|
| p(1) | $2.3 * 10^{-4}$ | $5.7 * 10^{-5}$ | $1.4 * 10^{-5}$ | $8.9 * 10^{-7}$ | $3.5 * 10^{-9}$ |
| p(2) | $2.6 * 10^{-8}$ | $1.6 * 10^{-9}$ | $1.0 * 10^{-10}$ | $3.9 * 10^{-13}$ | $6.0 * 10^{-18}$ |
| p(3) | $2.0 * 10^{-12}$ | $3.1 * 10^{-14}$ | $4.8 * 10^{-16}$ | $1.2 * 10^{-19}$ | $7.0 * 10^{-27}$ |
| p(2.3) | $1.1 * 10^{-4}$ | $2.8 * 10^{-5}$ | $7.1 * 10^{-6}$ | $4.4 * 10^{-7}$ | $1.7 * 10^{-9}$ |
| p(1,3) | | | | | |
| Total no. of oligonucleotides having freq. >1 | $28 * 10^3$ | $7.1 * 10^3$ | $1.1 * 10^3$ | 111 | 0.43 |

TABLE 3

Important facts

One chromosome contains on maximum $250 * 10^6$ base pairs (chromosome 1).
Number of 400 μm² dots/BCD is $10^5$.
Area of the BCD is $4.2 * 10^4$ mm².

TABLE 4

Number of n-mers and the total area of biobits.

| n | $4^n$ | Dot containing all n-mers as 100 μm² oligopixels | Dots/BCD |
|---|---|---|---|
| 4 | 256 | | |
| 5 | 1024 | | |
| 6 | 4096 | 0.4 mm² | $1.0*10^5$ |
| 7 | $16*10^3$ | 1.6 mm² | $2.5*10^4$ |
| 8 | $65*10^3$ | 6.5 mm² | $6.2*10^3$ |
| 9 | $260*10^3$ | 26 mm² | $1.6*10^3$ |
| 10 | $1.0*10^6$ | 100 mm² | |
| 11 | $4.2*10^6$ | 400 mm² | |
| 12 | $16.8*10^6$ | $1.6*10^3$ mm² | |
| 13 | $67.1*10^6$ | $6.4*10^3$ mm² | |
| 14 | $268*10^6$ | $26*10^3$ mm² | |
| 15 | $1.1*10^9$ | | |
| 16 | $4.3*10^9$ | | |

TABLE 5

Four quartets of dimeric oligonucleotides that can be used to construct subclasses of oligonucleotides

| 1 | 2 | 3 | 4 |
|---|---|---|---|
| AA | AC | AG | AT |
| CC | CG | CT | CA |
| GG | GT | GA | GC |
| TT | TA | TC | TG |

TABLE 6

One subclass of sixteen tetrameric oligonucleotides generated by using quartets 1 and 3 from Table 5.

| AA-AG | CC-AG | GG-AG | TT-AG |
|-------|-------|-------|-------|
| AA-CT | CC-CT | GG-CT | TT-CT |
| AA-GA | CC-GA | GG-GA | TT-GA |
| AA-TC | CC-TC | GG-TC | TT-TC |

What is claimed is:

1. A disk adapted for use in an analytical procedure requiring multiple reaction sites, said disk comprising:
   a disk body having a center portion and a perimeter;
   a plurality of first spiral channels located in said disk body, each of said first spiral channels extending from said center portion toward said perimeter to form a clockwise spiral pattern of channels in said disk body;
   a plurality of second spiral channels located in said disk body, each of said second spiral channels extends from said center portion toward said perimeter to form a counterclockwise spiral pattern of channels in said disk body, said first and second spiral channels intersecting at a plurality of locations to provide a plurality of reaction sites.

2. The disk according to claim 1 wherein said disk includes a centrally located circular fractionation zone for separating a mixture of nucleotides into separate fractions of nucleotides.

3. The disk according to claim 1 wherein one or more assay elements are located at a plurality of said reaction sites.

4. The disk according to claim 3 wherein said assay element includes an oligonucleotide or oligonucleotide analog.

5. The disk according to claim 4 wherein there are a sufficient number of reactions sites and a sufficient number of assay elements located at said reaction sites to provide for sequencing of a given unknown nucleotide sequence.

6. The disk according to claim 3 wherein said assay element includes a detector bead.

7. The disk according to claim 6 wherein said detector bead can be detected by an optical disk reader.

8. The disk according to claim 1 wherein said disk includes encoded information which is readable by an optical disk reader.

9. A disk adapted for use in an analytical procedure requiring multiple reaction sites, said disk comprising:
   an optical disk having a center portion and a perimeter;
   a plurality of first spiral channels located in said optical disk, each of said first spiral channels extending from said center portion toward said perimeter for form a clockwise spiral pattern of channels in said optical disk;
   a plurality of second spiral channels located in said optical disk, each of said second spiral channels extending from said center portion toward said perimeter to from a counterclockwise spiral pattern of channels in said optical disk, said first and second spiral channels intersecting at a plurality of locations to provide a plurality of reaction sites.

10. The disk according to claim 9 wherein one or more assay elements are located at a plurality of said reaction sites.

11. The disk according to claim 10 wherein said assay element includes an oligonucleotide or oligonucleotide analog.

12. The according to claim 10 wherein said analytical procedure is sequencing of DNA.

13. The disk according to claim 9 wherein said assay element includes a detector bead.

14. A disk adapted for use in an analytical procedure requiring multiple reaction sites, said disk comprising:
   a digital video disk having a center portion and a perimeter;

a plurality of first spiral channels located in said digital video disk, each of said first spiral channels extending from said center portion towards said perimeter for form a clockwise spiral pattern of channels in said compact disk;

a plurality of second spiral channels located in said digital video disk, each of said second spiral channels extending from said center portion toward said perimeter to from a counterclockwise spiral pattern of channels in said digital video disk, said first and second spiral channels intersecting at a plurality of locations to provide a plurality of reaction sites.

15. The disk according to claim 14 wherein one or more assay elements are located at a plurality of said reaction sites.

16. The disk according to claim 15 wherein said assay element includes an oligonucleotide or oligonucleotide analog.

17. The disk according to claim 16 wherein said analytical procedure is sequencing of DNA.

18. The disk according to claim 14 wherein said assay element includes a detector bead.

* * * * *

SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
      (A) LENGTH: 16
      (B) TYPE: nucleic acid
      (C) STRANDEDNESS: single-stranded DNA
      (D) TOPOLOGY: linear (ii) MOLECULE TYPE: oligonucleotide (xi) SEQUENCE DESCRIPTION: SEQ ID NO: 1:

GGTTAAAAAA AACCCC                                                    16

(2) INFORMATION FOR SEQ ID NO: 2:

(i) SEQUENCE CHARACTERISTICS:
      (A) LENGTH: 16
      (B) TYPE: nucleic acid
      (C) STRANDEDNESS: single-stranded DNA
      (D) TOPOLOGY: linear (ii) MOLECULE TYPE: oligonucleotide (xi) SEQUENCE DESCRIPTION: SEQ ID NO: 2:

CCCCAAAAAA AATTTT                                                    16

(2) INFORMATION FOR SEQ ID NO: 3:

(i) SEQUENCE CHARACTERISTICS:
      (A) LENGTH: 16
      (B) TYPE: nucleic acid
      (C) STRANDEDNESS: single-stranded DNA
      (D) TOPOLOGY: linear (ii) MOLECULE TYPE: oligonucleotide (xi) SEQUENCE DESCRIPTION: SEQ ID NO: 3:

GGTTAAAAAA AATTTT                                                    16

(2) INFORMATION FOR SEQ ID NO: 4:

(i) SEQUENCE CHARACTERISTICS:
      (A) LENGTH: 16
      (B) TYPE: nucleic acid

```
         (C) STRANDEDNESS: single-stranded DNA
         (D) TOPOLOGY: linear (ii) MOLECULE TYPE: oligonucleotide (xi) SEQUENCE DESCRIPTION: SEQ ID NO: 4:

CCCCAAAAAA AACCCC                                                            16

(2) INFORMATION FOR SEQ ID NO: 5:

(i) SEQUENCE CHARACTERISTICS:
         (A) LENGTH: 22
         (B) TYPE: nucleic acid
         (C) STRANDEDNESS: single-stranded DNA
         (D) TOPOLOGY: linear (ii) MOLECULE TYPE: oligonucleotide (xi) SEQUENCE DESCRIPTION: SEQ ID NO: 5:

GGGGAAAATT ATTAAAACCC GG                                                     22

(2) INFORMATION FOR SEQ ID NO: 6:

(i) SEQUENCE CHARACTERISTICS:
         (A) LENGTH: 22
         (B) TYPE: nucleic acid
         (C) STRANDEDNESS: single-stranded DNA
         (D) TOPOLOGY: linear (ii) MOLECULE TYPE: oligonucleotide (xi) SEQUENCE DESCRIPTION: SEQ ID NO: 6:

CCCCAAAAGG TGGAAAAGGG CC                                                     22
```